United States Patent
Kerrod et al.

(10) Patent No.: US 9,352,299 B2
(45) Date of Patent: May 31, 2016

(54) NEUTRAL, STABLE AND TRANSPARENT PHOTOCATALYTIC TITANIUM DIOXIDE SOLS

(71) Applicant: Cristal USA Inc., Hunt Valley, MD (US)

(72) Inventors: Julie Elizabeth Kerrod, Ulceby (GB); Anthony Roy Wagstaff, Scunthorpe (GB)

(73) Assignee: Cristal USA Inc., Hunt Valley, MD (US)

( * ) Notice: Subject to any disclaimer, the term of this patent is extended or adjusted under 35 U.S.C. 154(b) by 13 days.

(21) Appl. No.: 13/679,252

(22) Filed: Nov. 16, 2012

(65) Prior Publication Data
US 2013/0122074 A1 May 16, 2013

Related U.S. Application Data

(60) Provisional application No. 61/560,669, filed on Nov. 16, 2011.

(51) Int. Cl.

| | | |
|---|---|---|
| *B01J 21/06* | (2006.01) | |
| *B01J 35/00* | (2006.01) | |
| *B01J 37/00* | (2006.01) | |
| *A01N 59/16* | (2006.01) | |
| *B01J 37/03* | (2006.01) | |
| *B01J 37/04* | (2006.01) | |
| *B01J 37/08* | (2006.01) | |

(52) U.S. Cl.
CPC ............... *B01J 21/063* (2013.01); *A01N 59/16* (2013.01); *B01J 35/002* (2013.01); *B01J 35/004* (2013.01); *B01J 35/006* (2013.01); *B01J 37/036* (2013.01); *B01J 37/04* (2013.01); *B01J 37/08* (2013.01)

(58) Field of Classification Search
CPC ...... B01J 21/063; B01J 35/004; B01J 21/003; B01J 35/002
See application file for complete search history.

(56) References Cited

U.S. PATENT DOCUMENTS

| | | | |
|---|---|---|---|
| 5,049,309 A | 9/1991 | Sakamoto et al. | |
| 5,403,513 A | 4/1995 | Sato et al. | |
| 6,387,844 B1 * | 5/2002 | Fujishima et al. | 502/350 |
| 6,569,920 B1 | 5/2003 | Wen et al. | |
| 7,521,039 B2 | 4/2009 | Bygott et al. | |
| 7,605,186 B2 | 10/2009 | Chung et al. | |
| 7,763,565 B2 | 7/2010 | Fu et al. | |
| 7,879,757 B2 | 2/2011 | Kuroda et al. | |
| 2002/0160910 A1 * | 10/2002 | Sanbayashi et al. | 502/208 |
| 2006/0228476 A1 | 10/2006 | McCurdy | |
| 2007/0195259 A1 | 8/2007 | Olsson | |
| 2008/0081758 A1 | 4/2008 | Kuroda et al. | |
| 2009/0062111 A1 * | 3/2009 | Fu et al. | 502/170 |
| 2009/0209665 A1 | 8/2009 | Fu et al. | |
| 2009/0286676 A1 * | 11/2009 | Kim et al. | 502/216 |

FOREIGN PATENT DOCUMENTS

| | | |
|---|---|---|
| CA | 2201934 C | 3/2008 |
| CA | 2480736 C | 9/2008 |
| EP | 0737513 B1 | 5/2002 |
| EP | 1709125 | 4/2010 |
| EP | 1909971 B1 | 10/2010 |
| EP | 1497234 B1 | 11/2010 |
| EP | 1935929 B1 | 11/2011 |
| JP | 2002-179949 A | 6/2002 |
| JP | 2010-148999 A | 7/2010 |
| KR | 2003043536 A * | 6/2003 |
| WO | WO 2013/074984 A1 | 3/2013 |
| WO | WO 2013/074984 A1 | 5/2013 |

OTHER PUBLICATIONS

Mannion, Paul, "Pollution-busting laundry additive gets set to clean up" News, Sep. 26, 2012 (http://www.sheffield.ac.uk/news/nr/catclo-tony-ryan-london-college-fashion-air-purification-nanoparticles-1.211918) 3 pgs.

* cited by examiner

*Primary Examiner* — Frederick Krass
*Assistant Examiner* — Tracy Liu

(57) ABSTRACT

A method for preparing a neutral, stable and transparent photocatalytic titanium dioxide sol is provided. The method comprises (1) contacting an alkaline titanium dioxide sol with an alkaline peptizing agent to provide a peptized alkaline titanium dioxide sol; (2) neutralizing the peptized alkaline titanium dioxide sol; and (3) obtaining or collecting the neutral, stable and transparent photocatalytic titanium dioxide sol. The titanium dioxide sol is stable and transparent over a range of pH of about 7.0 to about 9.5. The titanium dioxide sol may include crystallites of titanium dioxide having an average particle size of less than about 10 nm with at least 90% of the crystallites being in the anatase form.

9 Claims, 14 Drawing Sheets

NEUTRAL, STABLE AND TRANSPARENT PHOTOCATALYTIC TITANIUM DIOXIDE SOLS

1. TECHNICAL FIELD

The presently disclosed and claimed inventive process(es), procedure(s), method(s), product(s), result(s) and/or concept(s) (collectively hereinafter referenced to as the "presently disclosed and claimed inventive concept(s)") generally relates to compositions imparting a photocatalytic coating on a surface. More specifically, the presently disclosed and claimed inventive concept(s) relates to sols of titanium dioxide nanoparticles that are useful for providing transparent photocatalytic coatings on a substrate which are depolluting and/or self-cleaning and may also have, in certain embodiments, anti-bacterial properties.

2. BACKGROUND

The photocatalytic properties of the semiconducting titanium dioxide material result from the promotion of electrons from the valence band to the conduction band under the influence of ultraviolet (UV) and near-UV radiation. The reactive electron-hole pairs that are created migrate to the surface of the titanium dioxide particles where the holes oxidize adsorbed water to produce reactive hydroxyl radicals and the electrons reduce adsorbed oxygen to produce superoxide radicals, both of which can degrade $NO_x$ and volatile organic compounds (VOCs) in the air. In view of these properties, photocatalytic titanium dioxide has been employed in coatings (both encased and unencased) and the like to remove pollutants from the air. Such coatings may also have the advantage of being self-cleaning since soil (grease, mildew, mold, algae, bacteria, etc.) is also oxidized on the surface.

In many applications, it is desirable for the titanium dioxide coating to be transparent in order to maintain the original appearance of the substrate (e.g., ceramic tile, paving block, brick, stone, marble siding surgical instruments used during medical procedures, solar cells, woven and non-woven fabrics of natural or synthetic fibers, etc.) or its original transparency (e.g., window glass, car windshield, surgical instruments used for viewing etc.). Titanium dioxide colloidal sols have proven to be useful precursor materials for forming such transparent and reactive coatings.

A stable alkaline titanium dioxide sol can be established at a pH above 11.30. The sol can be used for forming coatings that can be applied to buildings, concrete surfaces and roadways. However, the sol often at times has a strong and irritating pungent "ammonium type" smell and can be flammable under certain conditions. Thus, it is difficult to use such a sol without incurring the expense and difficulty of putting on personal protective equipment and the expense of employing extraction technology for removing residual amounts of sol from areas (such as ground soil) adjacent the substrate to be treated. In addition, the substrates may adversely react with the high pH peptizing agents that exist in the sol.

It is desirable to neutralize the alkaline titanium dioxide sol so that the sol will become virtually odorless and non-flammable-thereby overcoming many of the above-noted deficiencies, and allowing such a sol to be applied as an environmentally friendly photoactive water based surface coating. However, as the pH of the alkaline titanium dioxide sol is reduced the colloidal system typically agglomerates and becomes unstable and may even collapse. Such agglomeration is irreversible, that is, even if the solution is re-adjusted back to a high pH, colloidal stability is not returned. It is therefore desirable and long sought after in the art to provide stable neutral sols comprising photocatalytic titanium dioxide which are reactive, neutral and transparent. It is also desirable for such reactive, neutral and transparent photocatalytically active titanium dioxide sols to be stable over an extended period of time and also maintain photoactivity over a period of time and at a rate of activity that is above what is currently commercially available. It is well known to one of ordinary skill in the art that the creation of a stable, transparent and neutral $TiO_2$ sol is difficult (and has long been sought in the industry) because of the natural tendency of $TiO_2$ to flocculate between pH values of about 4 to about 10 due to the absence of any electrostatic stabilization occurring at neutral (or near neutral) pH. Furthermore, it is difficult to identify appropriate or effective molecules which can act as steric stabilizers in $TiO_2$ sols due to the extremely small particle size of the $TiO_2$. As effective steric stabilizers are generally larger molecules, one of ordinary skill in the art has found it difficult to identify appropriate steric stabilizers for use. It is also desirable for such reactive, neutral and transparent photocatalytically active titanium dioxide sols to exhibit anti-bacterial/anti-microbial activity. It is further desirable that the presently disclosed and claimed inventive concept(s) provide novel methods for preparing such reactive, neutral, stable and transparent sols which are readily implemented on a commercial scale.

SUMMARY OF THE INVENTION

In accordance with the foregoing objectives and others, it has been found that titanium dioxide sols, which are reactive, neutral, stable, transparent and which can be used safely and in an environmental friendly manner, may be formed by neutralizing alkaline titanium dioxide sols in the manner set forth herein.

In one aspect of the presently claimed and disclosed inventive concept(s), a method for preparing a reactive, neutral, stable and transparent photocatalytic titanium dioxide sol is provided, comprising: (1) reacting a hydrous titanium dioxide gel with an alkaline peptizing agent to provide a peptized alkaline titanium dioxide sol; (2) neutralizing the peptized alkaline titanium dioxide sol; and (3) obtaining or collecting the resulting neutral, stable and transparent photocatalytic titanium dioxide sol.

In another aspect of the presently claimed and disclosed inventive concept(s), a method for preparing a reactive, neutral, stable and transparent photocatalytic titanium dioxide sol is provided, comprising: (1) precipitating hydrous titanium dioxide from a solution having a titanium containing compound therein to form titanium dioxide particles; (2) forming a dispersion of the titanium dioxide particles in a liquid medium; (3) treating the dispersion with an alkaline peptizing agent to obtain a peptized alkaline titanium dioxide sol; (4) neutralizing the peptized alkaline titanium dioxide sol; and (5) obtaining or collecting the resulting neutral, stable and transparent photocatalytic titanium dioxide sol.

The peptized alkaline titanium dioxide sol can be neutralized by boiling the peptized alkaline titanium dioxide sol, mixing hydrogen peroxide with the peptized alkaline titanium dioxide sol, or mixing an acid compound with the peptized alkaline titanium dioxide sol. The acid compound may comprise for example, but not by way of limitation, a first acid compound and a second acid compound, wherein the first acid compound and the second acid compound can be selected from the group consisting of a mineral acid, an organic acid or combinations thereof.

The resulting sol of titanium dioxide is reactive, stable and transparent over a range of pH of about 8.5 to about 9.5. The stable colloidal titanium dioxide sol may be in a form of particles of titanium dioxide having an average size of less than about 50 nm, with crystallites less than about 20 nm, less than about 10 nm or between about 1 nm and about 10 nm, with the majority of the crystallites being in an anatase form. In one alternate embodiment, the crystallites may have an average particle size between about 1 nm and of about 5 nm. In accordance with another embodiment, at least 90% of the crystallites being in an anatase form.

The titanium dioxide of the presently claimed and disclosed inventive concept(s) is, in an embodiment, greater than 95% by weight in the anatase form. In other embodiments, the titanium dioxide particles of the presently claimed and disclosed inventive concept(s) have an average particle size of less than about 10 nm or, alternatively less than 5 nm.

In a further embodiment, the presently claimed and disclosed inventive concept(s) comprise titanium dioxide particles having an average particle size of less than about 50 nm, wherein the sol is transparent and is stable for at least 1 month when stored at room temperature. In other embodiments, the sol is stable when stored for at least 2, at least 3 or at least 4 months at room temperature. In yet another embodiment, the sol is stable when stored for at least 5 or at least 6 months at room temperature. In a further embodiment, the sol is stable when stored for at least 1 year or at least 2 years at room temperature. In a further embodiment the sol has a viscosity of less than about 100 centipoise after at least 4 weeks at room temperature.

Another aspect of the presently disclosed and claimed inventive concept(s) provides a neutral, stable and transparent photocatalytic titanium dioxide sol formed from an alkaline titanium dioxide sol which is peptized and neutralized.

Another aspect of the presently disclosed and claimed inventive concept(s) provides a structure or composition containing the reactive neutralized titanium dioxide sols for use on a substrate for NOx removal under UV exposure. The sols of the presently claimed and disclosed inventive concept(s) have longer stability as compared to commercially available sols having similar size and transparency profiles.

Another aspect of the presently disclosed and claimed inventive concept(s) provides an anti-bacterial composition comprising the neutral, stable and transparent photocatalytic titanium dioxide sol which, when placed in contact with bacteria, kills at least 80% of the bacteria.

These and other aspects of the presently claimed and disclosed inventive concept(s) will be better understood by reference to the following detailed description and accompanying figures.

DETAILED DESCRIPTION

Figure 1:
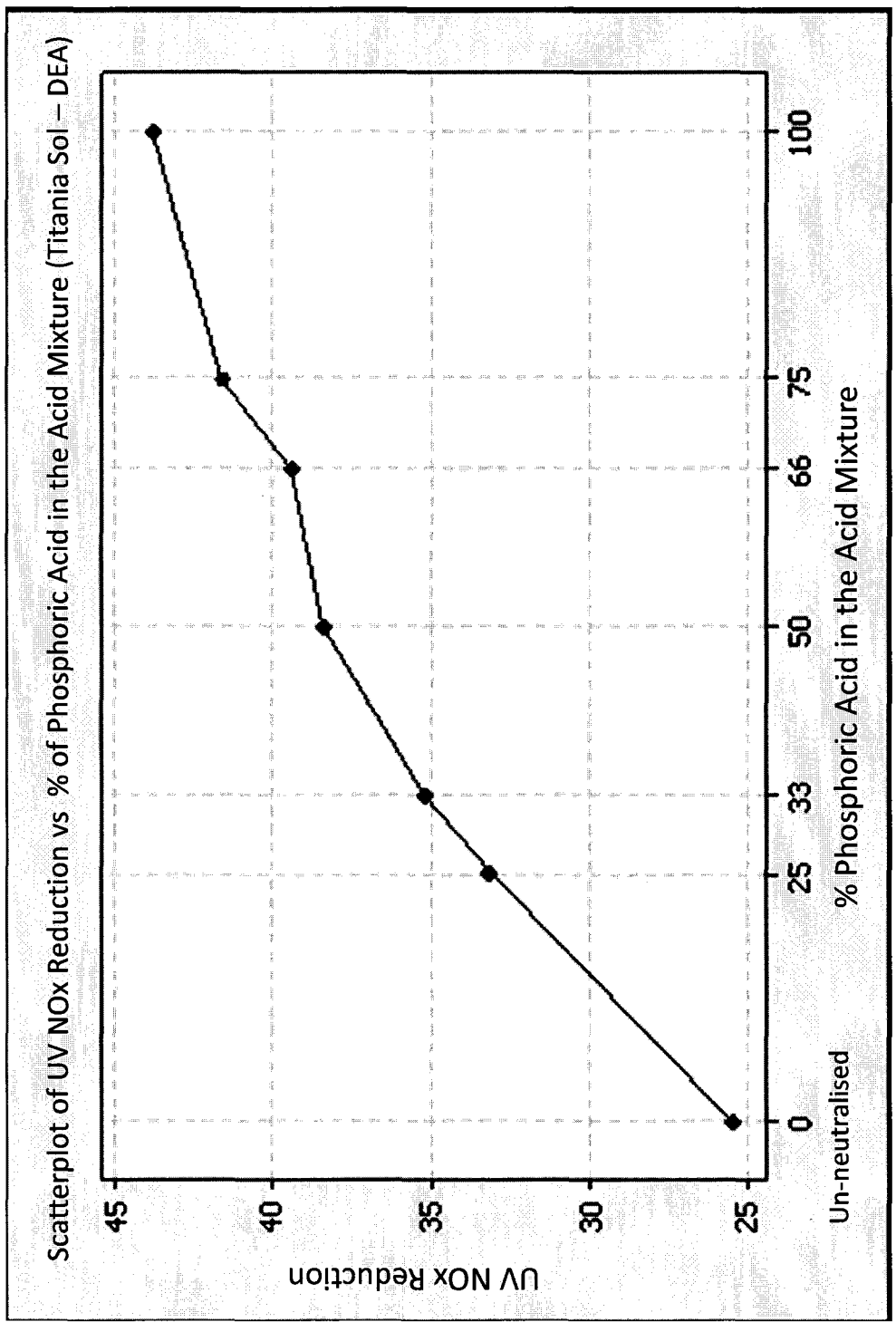
FIG. 1 is a graph comparing $NO_x$ reduction of an alkaline titanium dioxide sol containing DEA treated with different percentages of phosphoric acids combined with acetic acids under UV radiation.

Before explaining at least one embodiment of the inventive concept(s) disclosed herein in detail, it is to be understood that the presently disclosed and claimed inventive concept(s), process(es), methodology(ies) and/or outcome(s) is not limited in its application to the details of construction and the arrangement of the components or steps or methodologies set forth in the following description or illustrated in the drawings. The presently disclosed and claimed inventive concept(s), process(es), methodology(ies) and/or outcome(s) disclosed herein is capable of other embodiments or of being practiced or carried out in various ways. Also, it is to be understood that the phraseology and terminology employed herein is for the purpose of description and should not be regarded as limiting the presently disclosed and claimed inventive concept(s), process(es), methodology(ies) and/or outcome(s) herein in any way. With respect to any reference—patent or otherwise—mentioned herein, such reference should be considered to be incorporated by reference herein in its entirety as if set forth explicitly herein.

All terms used herein are intended to have their ordinary meaning unless otherwise provided. The term "sol" refers to a colloidal suspension of particles. The term "$NO_x$" refers to the species NO (nitrogen oxide) and $NO_2$ (nitrogen dioxide), either collectively or individually.

Where reference is made to "removal" of pollutants from the air, it will be understood to include complete or partial removal of pollutants from the air. Whether removal is "substantial" can be determined by the methods provided in the examples, where "substantial removal" refers to a reduction in the total concentration of a fixed amount of given pollutant by at least about 5%, preferably at least about 10%, and more preferably at least about 15%. Given the present disclosure (including the examples), one of ordinary skill in the art would appreciate that the sols of the presently claimed and disclosed inventive concept(s) provide exceptional NOx removal and/or degradation and, in one particular study, the sols of the presently claimed and disclosed inventive concept(s) provided 60% NO and 20% $NO_2$ removal under specific outdoor environmental conditions in London.

The method for preparing neutral, stable and transparent sols of colloidal photocatalytic titanium dioxide according to the presently disclosed and claimed inventive concept(s) generally comprises: (1) reacting a hydrous titanium dioxide gel with an alkaline peptizing agent to provide a peptized alkaline titanium dioxide sol; (2) neutralizing the peptized alkaline titanium dioxide sol; and (3) obtaining or collecting the resulting neutral, stable and transparent photocatalytic titanium dioxide sol which can be mainly in an anatase form and can have an average particle size of less than about 50 nm. In one embodiment, the average particle size of the titanium dioxide is less than or equal to about 20 nm. One of ordinary skill in the art will appreciate that the resulting neutral, stable and transparent photocatalytic titanium dioxide sol will be amorphous in nature.

In one embodiment, the alkaline peptizing agent is a mono-, di- or trialkyl amine; mono-, di- or triarylamines; organic bases with two or more functional groups such as dialkanolamines and trialkanolamines and the like. The mono-, di- or trialkylamine peptizing agents may comprise linear, branched or cyclic alkyl groups. Suitable amines include, but are not limited to, mono-, di- or trimethyl amine; mono-, di- or triethylamine; mono-, di- or tripropylamine; mono-, di- or tributyl amine, sec-butylamine, isobutylamine, isopropylamine, isoamylamine, tert-amylamine, 2-methylbutylamine, 1-methylbutylamine and combinations of the like. In one embodiment the alkaline peptizing agent is diethyl amine.

Amines with cyclic alkyl groups include, but are not limited to cyclopropylamine, cyclobutylamine, cyclopentylamine, cyclohexylamine, cycloheptylamine and cyclooctylamine as well as their di- and tri-alkyl derivatives. Of course, amines with different alkyl groups such as diisopropylethylamine, ethylbutylamine, methylethylamine, and the like, may be used. Also contemplated are cyclic amines such as pyrrolidine, piperidine, morpholine, and the like, as well as their N-alkyl derivatives. Preferably, bulky mono-, di- or tri-alkyl amines such as tert-butylamine, triethylamine, propylamine, dipropylamine, diisopropylethylamine, and the like, are used as basic peptizing agents.

In another embodiment, the alkaline peptizing agent can be a quaternary ammonium hydroxide. The quaternary ammonium hydroxide may, in one embodiment, be selected from the group consisting of tetraalkylammonium hydroxide where the alkyl contains one of $C_1$ through $C_{10}$ atoms or combinations of $C_1$ through $C_{10}$ atoms. The quaternary ammonium hydroxide can be tetralmethylammonium hydroxide.

The step of neutralizing the peptized alkaline titanium dioxide sol may be carried out by boiling the peptized alkaline titanium dioxide sol, mixing hydrogen peroxide with the peptized alkaline titanium dioxide sol, or mixing an acid compound with the peptized alkaline titanium dioxide sol. Boiling the peptized alkaline titanium dioxide sol can be conducted at a temperature to remove the alkaline peptizing agent. In one embodiment, the temperature is in a range of about 40° C. to about 120° C. In another embodiment, the temperature is in a range of about 60° C. to about 110° C.

Hydrogen peroxide may react with titanium dioxide to form a stable peroxo complex. Generally, a large amount of hydrogen peroxide is needed for neutralization to occur. In one embodiment, about 50% to about 200% of hydrogen peroxide is used based on the weight of the peptized alkaline titanium dioxide sol. In another embodiment, about 100% to about 150% of hydrogen peroxide is used based on the weight of the peptized alkaline titanium dioxide sol. One of ordinary skill in the art, given the present disclosure, would understand that any specific percentage of hydrogen peroxide may be used to long as the neutralization occurs.

The acid compound can, in one embodiment, be selected from a group consisting of a first acid compound, a second acid compound and combinations thereof. The first acid compound can, in one embodiment, be selected from a mineral acid, an organic acid and combinations thereof. In one embodiment, the mineral acid is phosphoric acid. The organic acid can, in one embodiment, be an aliphatic, aromatic hydroxycarboxylic acid or combinations thereof. The organic acid can be selected from the group consisting of oxalic acid, citric acid, tartaric acid, salicylic acid and combinations thereof, for example.

The second acid compound can be a mineral acid, an organic acid or combinations thereof. In one embodiment, the mineral acid is nitric acid. When an organic acid is used, it can be acetic acid. The percentage of the first acid compound can be varied from about 25 to about 100 parts by weight and the percentage of the second acid compound can be varied from about 0 to about 75 parts by weight and one of ordinary skill in the art would appreciate and be capable of adapting such parts by weight as necessary.

In a particular embodiment, the acid compound is added drop wise to the peptized alkaline titanium dioxide sol while stirring at room temperature. The stirring may be done continuously or intermittently as long as the functional requirement is met. The final pH value of the resulting neutralized sol is, in a certain embodiment, controlled so as to be within a range of about 8 to about 9.

In another aspect of the presently claimed and disclosed inventive concept(s), a method for preparing a neutral, stable and transparent photocatalytic titanium dioxide sol is provided, comprising: (1) precipitating hydrous titanium dioxide from a solution having a titanium containing compound therein to form titanium dioxide particles; (2) forming a dispersion of the titanium dioxide particles in a liquid medium; (3) treating the dispersion with an alkaline peptizing agent to obtain a peptized alkaline titanium dioxide sol; (4) neutralizing the peptized alkaline titanium dioxide sol; and (5) obtaining or collecting the resulting neutral, stable and transparent photocatalytic titanium dioxide sol.

The titanium containing compound may be any compound capable of forming a precipitate of titanium dioxide. In one embodiment, the titanium containing compound is an organotitanium compound. Suitable organotitanium compounds include, but are not limited to, titanium alkoxides of the general structure $Ti(OR)_4$ where each R is independently alkyl, aryl or heteroaryl; titanium acyl compounds such as titanyl acetylacetonate and the like. Preferred titanium alkoxides include titanium tetraisopropoxide, titanium tetra-n-propoxide, titanium tetraethoxide, titanium tetramethoxide, titanium tetra-n-butoxide and titanium tert-butoxide and the like. Mixed titanium alkoxides, where the R groups in $Ti(OR)_4$ may be different, are also contemplated as the titanium containing compound. Other suitable organic titanium compounds include titanium (IV) amine compounds such as tetrakis(dimethylamino)titanium, tetrakis(diethylamino)titanium and the like.

Titanium halides represented by the formula $TiX_4$, where X is chloro, bromo, iodo or fluoro, or mixtures thereof, may also be used as titanium containing compounds. The presently claimed and disclosed inventive concept(s) also contemplates the use of organotitanium halides such as chlorotitanium triisopropoxide $(Ti(O-i-Pr)_3Cl)$ and the like as titanium containing compounds. Organotitanium di- and tri-halides are also contemplated. Although not being bound by theory, it is believed that when titanium halides are used as titanium containing compounds, the halides are typically first hydrolyzed in a controlled fashion to a less reactive species such as titanium oxyhalide (i.e. titanium oxychloride and the like). The resulting intermediate titanium species may then be further hydrolyzed to $TiO_2$ by adjusting the pH of the solution.

In another aspect of the presently claimed and disclosed inventive concept(s), the titanium containing compound may be a water-soluble titanium salt. Suitable titanium salts include, but are not limited to, titanium oxychloride, titanium sulfate, titanium oxynitrate and the like. Precipitation of $TiO_2$ from water-soluble salts may be affected by adjusting the pH of the solution to a pH where the water soluble titanium salt will hydrolyze and form $TiO_2$, which precipitates from solution. Typically, this is accomplished by raising the pH of the solution with addition of a base compound such as NaOH, for example, but not by way of limitation.

The solution of the titanium containing compound may be an aqueous solution or may comprise a suitable organic solvent added to water to achieve hydrolysis of the titanium containing compound. Mixtures of water and an organic solvent may also serve to control the rate of hydrolysis of the titanium containing compound and the precipitation of $TiO_2$. If organic solvents are used, the solvents will typically be miscible with water or will have sufficient solubility for water so that sufficient water will be available to hydrolyze the titanium containing compound to $TiO_2$. Suitable organic solvents include alcohols such as methanol, ethanol, isopropanol and the like; amides such as dimethylformamide and dimethylacetamide and the like; and sulfoxides such as dimethylsulfoxide. There is essentially no constraint on the concentration of the solution of the titanium containing compound, although it is preferably suitably concentrated such that the kinetics of the precipitation are optimized.

Precipitation may be affected by any suitable method, including without limitation, hydrolysis, pH adjustment, or solvent-shifting. The precipitation method employed will be determined largely by the selection of titanium containing compound. For example, hydrolysis is the preferred precipitation method where the titanium containing compound is a titanium alkoxide or titanium acetylacetonate. For titanium oxychlorides or titanium sulfates, which are water soluble, precipitation is best carried out by pH adjustment (e.g., raising the pH) or by adding a solvent in which the compound is essentially insoluble, such as acetone or higher alcohols ("solvent shifting"). By "essentially insoluble" is meant that the solubility of the titanium containing compound is sufficiently low in the solvent to permit titanium dioxide to precipitate from solution when contacted with the second solvent. By "higher" alcohols is meant $C_5$ alcohols or greater, including, without limitation, pentanol, hexanol, heptanol, octanol, for example.

In one embodiment, the titanium containing compound is mixed with an alcohol. As the titanium containing compound is hydrolyzed, it forms $TiO_2$ which precipitates as amorphous $TiO_2$ particles with an average particle size of less than about 50 nm. In another embodiment, the titanium containing compound is mixed with a chelating base to form a chelated titanium species and the mixture is then added to water to hydrolyze the titanium containing compound and precipitate amorphous $TiO_2$.

Any base known to those in the art that will increase the pH of the water solution of the water-soluble titanium salt may be used to precipitate $TiO_2$, including inorganic and organic bases. Suitable bases include, but are not limited to, amine bases including as ammonium hydroxide, mono-, di- or tri-alkylamines such as triethylamine, diisopropylethylamine and the like; cyclic amine bases such as N-ethylmorpholine, piperidine, pyrrolidine and the like; hydroxides or alkoxides of alkali metals or alkaline earth elements such as sodium, lithium, potassium hydroxide, magnesium hydroxide, calcium hydroxide; sodium, lithium or potassium alkoxides such as methoxide, ethoxide, butoxide, t-butoxide and the like; carbonate and bicarbonate bases such as sodium, lithium or potassium carbonate and bicarbonate and the like. It will be apparent to skilled persons that the type of base is not limited to the bases described above and that there are many other bases that may be used to adjust the pH of the solution of water-soluble titanium salt.

Alternatively, the $TiO_2$ may be precipitated from solution by changing the composition of the solvent so that the $TiO_2$ is no longer soluble. In this embodiment, a titanium containing compound which is in solution in a suitable solvent may be added to a second "anti-solvent" in which the precursor is not soluble. For example, this may be achieved by adding a titanium containing compound in a water-miscible organic solvent such as acetone or higher alcohols to water. Alternatively, the precipitation may be accomplished by adding a water-miscible organic solvent to an aqueous solution of the water soluble titanium salt to lower the solubility of $TiO_2$. The titanium precipitate formed may be used in the next step of the process, whether it is partially hydrolyzed or fully hydrolyzed to $TiO_2$.

In certain aspects of the invention, the controlled hydrolysis or controlled precipitation of the titanium containing compound is achieved by treating the titanium containing compound with a chelating agent, which forms stable chelate bonds with titanium in aqueous solution, prior to hydrolysis of the titanium containing compound and precipitation of $TiO_2$. Using the chelating agents, the rate of hydrolysis or precipitation of the titanium containing compound in water may be controlled, thereby controlling the particle size of the $TiO_2$ particles formed.

In the presently disclosed and claimed inventive concept(s), a neutral or base chelating agent can be used. Suitable neutral chelating agents include dicarbonyl compounds such as a diketone, a diester, a ketoester and the like. Diketone chelators include 2,4-pentanedione, 1,4-hexanedione, 1,3-pentanedione, 2,4-hexanedione, and dipivaloyl methane. Diester chelators include mono or di-alkyl esters of dicarboxylic acids. Suitable diesters include dialkyl malonates, such as dimethyl and diethylmalonates and the like.

Ketoester chelators include, but are not limited to, alkyl acetoacetates such as methyl acetoacetate, ethyl acetoacetate, isopropyl acetoacetate, butyl acetoacetate and the like. Mixtures of two or more dicarbonyl chelators may also be used to prepare the inventive sols.

Base chelating agents include organic bases that comprise two or more functional groups that are able to chelate to the titanium atom. Suitable chelating agents include dialkanolamines and trialkanolamines such as diethanolamine, triethanolamine and the like. Other suitable chelating bases with two or more functional groups include ethylenediamine, diethylenetriamine, triethylenetetramine, 2,2'-bipyridine, 1,10-phenanthroline, ethylenediaminetetraacetic acid or -tetraacetate, ethylenediaminetriacetic acid or -triacetate, 2,2',2"-terpyridine, 1,4,7-triazacyclononane, tris(2-aminoethyl) amine, and the like.

Addition of a base chelating agent to the titanium containing compound results in a more stable species prior to precipitation, and can reduce the degree of hydrolysis thereby facilitating the peptization of the titanium particles in the next step. In one embodiment, the base used to treat the titanium containing compound is the same base used as an alkaline peptizing agent. The amount of chelating base added to the titanium containing compound is such that the molar ratio of base to titanium may be, in one embodiment, ≤0.5:1. In another embodiment, the molar ratio of base to titanium may be ≤0.3 or 0.2:1.

When a soluble titanium salt is used as a titanium containing compound and an organic base is used as an alkaline peptizing agent, a de-ionizing step may alternatively be used to reduce the concentration of ions present in the titanium containing compound prior to the precipitation step. Lowering the concentration of the ions in the solution facilitates the chelation of the titanium with chelating agents. Any method that will reduce the level of ions in the soluble titanium salt solution may be used, including treatment with an anion exchange resin, precipitation of insoluble salts, and the like.

In one embodiment, the titanium containing compound is treated with an anionic ion exchange resin to remove excess ions that may be in the solution of the titanium containing compound such as sulfate ions, chloride ions, and the like, depending on the nature of the soluble titanium salt. When the soluble titanium salt solution is treated with an ion exchange resin, the pH of the solution will typically increase over time and may result in the formation of a $TiO_2$ precipitate. Preferably, the treatment time of the soluble titanium salt with an anion exchange resin will be limited so that the pH of the solution is maintained at less than about 3 in order to prevent formation of a $TiO_2$ precipitate. More preferably, the de-ionization treatment will be limited so that the pH of the solution is maintained at less than about 2. Once the level of ions is reduced, the titanium salt solution is separated from the ion exchange resin and treated with a base that is capable of forming a chelating bond, as described above. The pH of the solution of the chelated titanium dioxide salt is then adjusted with a suitable base to form $TiO_2$ which precipitates from solution.

The precipitated $TiO_2$ may be collected by any suitable means including decanting, centrifugation and filtration. The isolated solid may optionally be washed with water to remove byproducts of the hydrolysis reaction and other impurities prior to the dispersion step in a liquid medium.

In one embodiment, the precipitated $TiO_2$, which is in an amorphous form, is generally collected by filtration and thoroughly washed with de-ionized water prior to re-dispersion. The washed, wet filter cake is then re-dispersed in a volume of de-ionized water with vigorous agitation (e.g., stirring with a deep vortex, shaking, etc.). The de-ionized water typically, although not always, comprise alkaline peptizing agents in solution before the dispersion is formed. Since the benefit of the alkaline peptizing agent is largely realized during the subsequent thermal treatment step, it is not strictly necessary that the alkaline peptizing agent be present in the aqueous solution before the precipitate is re-dispersed. Rather, the alkaline peptizing agent may also be added after the dispersion is formed, or may be added to the titanium containing compound before the precipitation is carried out or, it may be added during or throughout each or both steps. The amount of de-ionized water used will be such that the weight ratio of the initial titanium containing compound (e.g. titanium isopropoxide) to the total weight of the dispersion is from about 1:2 to about 1:10, from about 1:3 to about 1:6, and from about 1:4 to about 1:5.

The concentration of the $TiO_2$ in the dispersing liquid determines the initial concentration of the sol after peptization. The $TiO_2$ sols can be further diluted or concentrated, if desired, after the peptization step is complete. Typically, a $TiO_2$ dispersion of about 1% to about 30% of $TiO_2$ by weight in an aqueous solvent will be used for the peptization step. The aqueous solvent may be any solvent or solvent mixture that comprises water. For example, mixtures of water and a water-miscible solvent such as an alcohol may be used. More typically, the concentration of the dispersion is from about 2% to about 15% or from about 5% to about 15% by weight of the mixture. In one embodiment, the concentration is from about 8% to about 12% or from about 5% to about 10% by weight.

The precipitated $TiO_2$ is thereafter treated with an alkaline peptizing agent with agitation to form the $TiO_2$ sols of the presently claimed and disclosed inventive concept(s). The dispersed $TiO_2$ may be treated with the alkaline peptizing agent at room temperature or at an elevated temperature or range of elected temperatures with agitation until the dispersion forms a transparent or translucent mixture. A wide variety of alkaline peptizing agents may be used in the presently disclosed and claimed inventive concept(s). The alkaline peptizing agents used here with regard to this step are the same as those described previously.

The peptization is typically carried out at a temperature of from about 70° C. to about 150° C. (i.e., a thermal treatment) for a period of time from about 3 hours to about 3 days under continuous or intermittent agitation. It is not necessary to neutralize the solution prior to any thermal treatment. Therefore, in one embodiment, the dispersion comprising the alkaline peptizing agent is not subject to a neutralization step, such as by the addition of a basic solution, prior to or during the thermal treatment. It has also been found useful, in one embodiment, to perform the peptization in a sealed hydrothermal reactor due to the concomitant increase in pressure. Bomb-type hydrothermal reactors, such as those available from Parr Instruments (Illinois), have been found suitable for use in the hydrothermal reaction for example, but not by way of limitation. One or more bomb reactors may be placed in a roller oven or the like to provide the thermal conditions and to achieve agitation. The resulting alkaline titanium dioxide sol can be neutralized by boiling the sol, mixing hydrogen peroxide with the sol, or mixing an acid compound with the sol. All these neutralization methods are the same as those described previously.

In accordance with another embodiment of the invention, a neutral, stable and transparent photocatalytic titanium dioxide sol can be formed from an alkaline titanium dioxide sol which is peptized and neutralized. The alkaline titanium dioxide sol can be peptized with an alkaline peptizing agent as described above, thereby forming a peptized alkaline titanium dioxide sol which can be neutralized by an acid compound as described above, thereby forming the neutral, stable and transparent photocatalytic titanium dioxide sol.

The neutral, stable, transparent or translucent $TiO_2$ sols can contain from about 0.5% to about 40% of $TiO_2$ by weight in an aqueous solvent. More typically, the sols can contain from about 2% to about 20% or from about 2% to about 15% or between about 5% to about 20% or between about 5% to about 15% titanium dioxide by weight. In one embodiment, the sols can contain between about 8% to about 12% or about 5% to about 10% $TiO_2$ by weight of the mixture. In accordance with another embodiment, the neutral, stable, transparent or translucent $TiO_2$ sols can contain from about 20% to about 40% or between about 25% to about 40% or between about 30% to about 40% titanium dioxide by weight.

The neutral, stable, transparent or translucent $TiO_2$ sols can contain at least about 10% or at least 15% or at least 16% or at least 17% or at least 18% or from about 10% to about 20% or from about 12% to about 16% or at least 16% to about 18% alkaline peptizing agent based on the combined weight of the alkaline peptizing agent and the $TiO_2$.

When the alkaline peptizing agent is present in the neutral, stable, transparent or translucent $TiO_2$ sol(s) in an amount of at least about 7% based on the combined weight of the alkaline peptizing agent and the $TiO_2$, the resulting peptized alkaline titanium dioxide sol can be neutralized with an acid comprising phosphoric acid. Further, the neutral, stable, transparent or translucent $TiO_2$ sol(s) can contain from about 5 to about 20 or from about 30 to about 40 wt % titanium dioxide.

When the alkaline peptizing agent is present in the neutral, stable, transparent or translucent $TiO_2$ sol(s) in an amount of at least about 18% based on the combined weight of the alkaline peptizing agent and the $TiO_2$, the resulting peptized alkaline titanium dioxide sol can be neutralized with a combination of phosphoric acid and acetic acid; wherein the weight ratio of the phosphoric acid to the acetic acid can be in the range of from about 0.8:1 to about 1.2:1 or from about 0.9 to about 1.1 or about 1:1. The phosphoric acid and the acetic acid can be substantially simultaneously added to the peptized alkaline titanium dioxide sol. Further, the neutral, stable, transparent or translucent $TiO_2$ sol(s) can contain from about 5 to about 20 or from about 30 to about 40 wt % titanium dioxide.

The peptized alkaline titanium dioxide sol or the neutral, stable and transparent photocatalytic titanium dioxide sol can also be washed with demineralized water such that the concentration of calcium and sodium ions is less than about 71 ppm and less than about 13 ppm, respectively, in the resulting washed material. The resulting filtrate conductivity can be equal to or less than 500 μs. The viscosity of the resulting washed peptized alkaline titanium dioxide sol or of the washed neutral, stable and transparent photocatalytic titanium dioxide sol can be less than about 100 centipoise after at least 4 weeks at room temperature.

The neutral, stable and transparent photocatalytic titanium dioxide sol(s) are reactive, stable and transparent over a range of pH of about 7 to about 9.5. The average particle size of the neutral, stable and transparent photocatalytic titanium dioxide sol(s) after neutralization will generally be less than about 50 nm although one of ordinary skill in the art will appreciate that some amount of the process may have a particle size>about 50 nm without effecting the presently claimed and disclosed inventive concept(s) outlined herein. More typically, the average particle size of the titanium dioxide particles will be less about 30 nm, 20 nm or 10 nm. In one embodiment, the crystallite size of the titanium dioxide sol will be less than about 5 nm. Reference herein to the size of titanium dioxide particles will be understood to mean the average particle size of the titanium dioxide particulates. Where the particle size is modified by the term "about," (and as the term is used elsewhere therein) it will be understood to embrace somewhat larger or smaller particles sizes than the indicated value to account for experimental errors inherent in the measurement and variability between different methodologies for measuring particle size (or temperature, pressure, pH or time, for example), as will be apparent to one skilled in the art. The diameters may be measured by standard particle size analysis techniques, for example, transmission electron microscopy (TEM, XRD) or by light scattering techniques (e.g., without limitation, dynamic light scattering, by Malvern Instruments Ltd., U.K.).

Alternatively, the particles may be characterized by surface area. Typically, the titanium dioxide used in the sols of the presently claimed and disclosed inventive concept(s) will have a surface area, as measured by any suitable method, including 5-point BET on a dried sample, of greater than about 20 $m^2/g$. More typically, the photocatalytic titanium dioxide particles have surface areas of greater than about 50 $m^2/g$ or greater than about 70 $m^2/g$. In one embodiment, the titanium dioxide particles have surface areas greater than about 100 $m^2/g$. In another embodiment, the surface areas are greater than about 150 $m^2/g$. In yet another embodiment, the titanium dioxide particles will have a surface area greater than about 200 $m^2/g$, greater than about 250 $m^2/g$, or greater than about 300 $m^2/g$.

The sols according to the presently claimed and disclosed inventive concept(s) may optionally include additional ingredients provided that the addition of such ingredients does not have a measurable negative impact on either the transparency or stability of the sol. For example, it is contemplated that the sols can include minor amounts of bactericidal agents, organic solvents (e.g. alcohols), film-forming aids, sequestering agents, pH adjusters, without limitation. In one embodiment, the sols will be substantially free of metal ions chosen from group I-VA, and the lanthanide or actinide series of the periodic table, by which is meant that no additional amounts of such metal ions are added to the sols or intermediate preparations beyond any trace amounts which are present as impurities in the titanium starting material or other reagents.

While the sols according to the presently claimed and disclosed inventive concept(s) are transparent, it has also advantageously been found that the sols form films that, when applied to a substrate, are also transparent. Included in the presently claimed and disclosed inventive concept(s) is therefore a method of forming a transparent photocatalytic de-polluting, self-cleaning film or coating on a substrate by applying to the substrate the sols according to the presently claimed and disclosed inventive concept(s). Generally, the films are allowed to dry on the substrate to a transparent coating having suitable adhesion to the substrate for use in the particular application or environment to which it is put. There is essentially no limit on the nature of the substrate to which the sols of the presently claimed and disclosed inventive concept(s) can be applied. Cement, metal, glass, polymeric, wood, ceramic, paper, textile, and leather substrates are each contemplated to be suitable for example, but not by way of limitation.

The stable, transparent sols of the presently claimed and disclosed inventive concept(s) will find particular utility in any application where photocatalytic activity is desired. Due to the transparent nature of the sols, they are ideally suited for coating surfaces or structures which are themselves transparent (i.e., glass) or for providing a coating that does not alter the appearance of the underlying substrate. Notable applications include, without limitation, photocatalytic coatings for air de-pollution on road surfaces, pavers and ceramic tiles, building exteriors, window glass, car windshields and the like. The sols of the presently claimed and disclosed inventive concept(s) will also find utility on fabrics, furniture, art works, for example, due to their self-cleaning properties. Such activity also imparts substitutates treated with the sols of the presently claimed and disclosed inventive concept(s) with a "stain-less" or "stain-free" or "stain-repellent" character. Additionally, the sols of the presently claimed and disclosed inventive concept(s) also provide UV-protection to the substrates to which they are applied. In a particular embodiment, for example but not by way of limitation, the sols of the presently claimed and disclosed inventive concept(s) can be coated on clothing or other items capable of being worn or disposed about a mammal such as a human. The clothing having the sols coated thereon would effectively block emitted X-rays from reaching through the clothing and interacting with the bodily tissues. In this manner, a protective garment or drape can be worn by an X-ray technician or laboratory worker and thereafter provide a level of protection from X-rays or other UV radiation.

Further, a structure with a titanium dioxide-containing layer can comprise a substrate and a substantially anatase titanium dioxide-containing layer on the surface of the substrate, wherein the transparency of the titanium dioxide-containing layer at visible light wavelength of 400-700 nm can be from about 65% to about 95% and the titanium dioxide-containing layer can be formed from the neutral, stable and transparent photocatalytic titanium dioxide sol(s) described above. The thickness of the titanium dioxide-containing layer can be about 0.1-1.5 μm. The structure can also exhibit an initial amount of $NO_x$ removal from air in proximity to the titanium dioxide-containing layer of at least about 80%, or of at least about 75% after about 450 days.

The stable, transparent titanium dioxide sol of the presently claimed and disclosed inventive concept(s) has a photocatalytic effect that also has oxidoreductive functionality and thereby is capable of decomposing harmful constituents and also provides antibacterial properties to the coated substrate when irradiated with lights such as sunlight and/or an ultraviolet light source. Thus, coatings containing the stable and transparent dioxide sols of the presently claimed and disclosed inventive concept(s) or substrates coated with such sols have antibacterial properties. Further, such sols impart a deodorizing effect and are capable of reducing noxious fumes in the area adjacent the sols or substrates coated with such sols.

In accordance with another embodiment, an anti-bacterial composition can comprise any of the neutral, stable and transparent photocatalytic titanium dioxide sol(s) described herein; wherein the anti-bacterial composition, when placed in contact with bacteria, can kill at least 80% or at least 90% of the bacteria. The anti-bacterial composition can be used as a partial or complete coating on a device, such as but not limited to a medical device. Further, the photocatalytic anti-bacterial activity of the anti-bacterial composition, when placed in contact with the bacteria, is at least about 2 or at least about 3; wherein the photocatalytic antibacterial activity is determined in accordance with the formula:

$$\log(B_L/C_L) - \log(B_D/C_D);$$

and wherein
$B_L$=mean bacterial count on a control surface not coated with the anti-bacterial composition after X hours light exposure;
$C_L$=mean bacterial count on a test surface coated with the anti-bacterial composition after X hours light exposure;
$B_D$=mean bacterial count on a control surface not coated with the anti-bacterial composition after X hours darkness;
$C_D$=mean bacterial count on a test surface coated with the anti-bacterial composition after X hours darkness; and
X ranges from about 14 to about 24 hours.

The sol based photocatalytic coating of the presently claimed and disclosed inventive concept(s) can also be doped with a metal to kill bacteria adhered to the surface. The metal, for example, but not by way of limitation, is selected from the group consisting of Ag, Zn, Mg, Sn, Fe, Co, Ni, Se, Ce, Cu and combinations thereof. Doping of the photocatalytic coating with the metal can be carried out by adding a soluble salt of the metal to the titanium sol. The metal salt can be a nitrate, a sulfate or a chloride, for example, but not by way of limitation. The amount of the metal salt added is generally about 0.01% to about 1% of the titanium compound by mole quantity although one of ordinary skill in the art would appreciate that greater amounts may be used depending upon the use to which the sol or photocatalytic coating will be put. The resultant solution which the doped metal can be used to form the photocatalytic coating(s) described hereinabove. In one embodiment for example, the photocatalytic coatings of the presently claimed and disclosed inventive concept(s) (with or without metal doping) inhibit and/or are resistant to the colonization of Methicillin-resistant *Staphylococcus aureus* (MRSA).

Alternatively, after forming the photocatalytic coating, a soluble salt of the metal can be applied thereon and the resulting coating can thereafter be subjected to irradiation or light emission in order to deposit the metal by photoreduction. The metal doped photocatalytic coating is capable of killing bacteria adhered to the surface. Moreover, such a metal doped photocatalytic coating can further inhibit the growth of microorganisms such as mold, algae and moss for example, but not by way of limitation. As a result, the surface of a building, a machine, apparatus, household, article and the like can be maintained clean, substantially without bacterial colonization over an extended period of time. As such, the sols of the presently claimed and disclosed inventive concept(s) have commercial applicability to the construction restoration and medical industries, for example, but not by way of limitation.

EXAMPLES

The following examples are presented to aid in an understanding of the presently claimed and disclosed inventive concept(s) and are not intended to, and should not be construed to limit the presently claimed and disclosed inventive concept(s) in any way. All alternatives, modifications and equivalents that may become obvious to those of ordinary skill in the art upon a reading of the present disclosure are included within the spirit and scope of the presently claimed and disclosed inventive concept(s) and should be considered as being expressly included herein.

Example 1

200 g of un-neutralized titania sol having product designation CristalACTiv™ manufactured by Cristal Global (in which titania was in a weight % of 17.5±2.5 at a pH of 11.5±1) and diethyl amine as an alkaline peptizing agent were placed into a baffled mixing container and stirred using an impellor mixer, to provide movement and agitations throughout the whole volume. A pH probe was positioned to provide readings of the mixed solution. The acid mixtures of 5M phosphoric acid and 5M acetic acid were prepared. 100 g of each acid mixture were made and labeled according to the % (by mass) of the amount of 5M phosphoric acid in the mixture as shown in Table 1.

TABLE 1

Acid Compositions

| Mix Label | g, 5M Phosphoric acid | g, 5M Acetic acid |
|---|---|---|
| 25% | 25 | 75 |
| 33% | 33 | 67 |
| 50% | 50 | 50 |
| 66% | 66 | 34 |
| 75% | 75 | 25 |
| 100% | 100 | 0 |

The acid mixture was added at a substantially constant rate (about 0.5-0.7 g/min) equivalent to 0.25-0.35% of the sol mass per minute. Acid addition was slowed when a pH value of about 9.0 was reached so as to obtain a final pH of 8.5. When pH=8.5 was obtained, acid addition was stopped, and mixing continued for at least about 60 minutes. During this period of time the pH increased slightly to approximately 8.7 to 8.9 Thus, small additions of acid were made as required in order to adjust the pH back to 8.5. About 5.5% of the acid mixture was added based on the weight of the alkaline titanium dioxide sol. The content of titanium dioxide was about 15 wt % and the content of diethyl amine was about 2.5 wt %, each based on the total weight of the neutralized titanium dioxide sol. The viscosity of the neutralized titanium dioxide sol was measured to be about 18 cps. The surface area, measured by BET, of a sample of the product as later dried was >250 m$^2$/g.

Example 2

Figure 2:
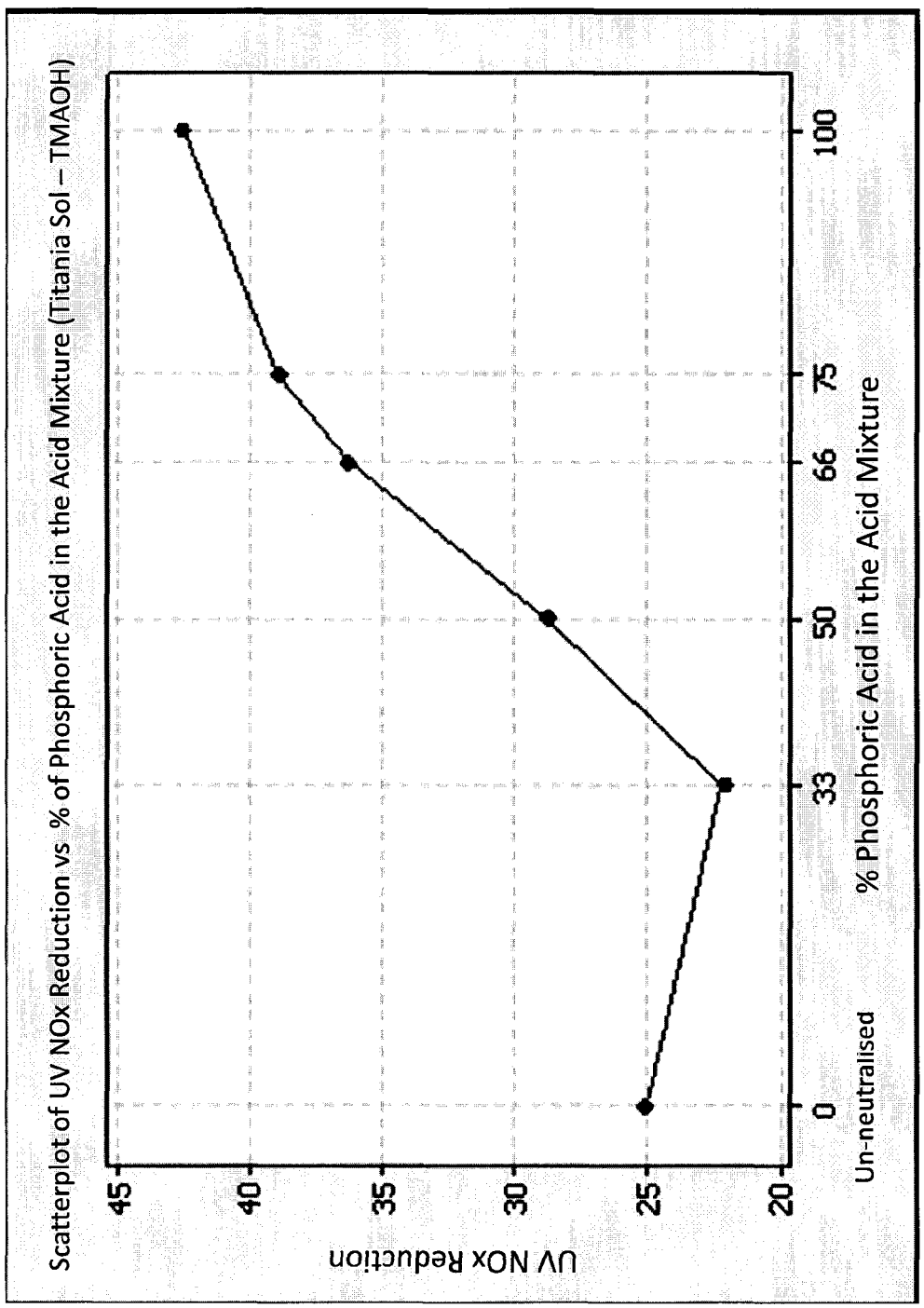
FIG. 2 is a graph comparing $NO_x$ reduction of an alkaline titanium dioxide sol containing TMAOH (tetramethylammonium hydroxide) treated with different percentages of phosphoric acids combined with acetic acids under UV radiation.

In order to investigate the photocatalytic activity of coatings prepared from the sols according to the presently claimed and disclosed inventive concept(s), the neutralized sols of Example 1, as well as a similarly prepared titania sol as that of Example 1 but containing tetramethylammonium hydroxide (TMAOH) instead of diethylamine, which were each neutralized with various mixtures of phosphoric and acetic acids (as described in Table 1), were deposited on test strips of 15 mm×100 mm cut out from Whatman 541 filter paper. About 0.05 g to about 0.0520 g of the neutralized sols on areas of about 5 to about 5.2 g/m$^2$, was added to each test strip. Each test strip was dried for 24 hours before NO$_x$ testing. The methodology for determining NO$_x$ reduction was substantially as described in U.S. Patent Pub. 2007/0167551, the disclosure of which is hereby incorporated by reference in its entirety. Briefly, the test samples were placed in an air-tight sample chamber and sealed. The sample chamber was in communication with a three channel gas mixer (Brooks Instrument, Holland) through which NO (nitrogen oxide), NO$_2$ (nitrogen dioxide), and compressed air containing water vapor were introduced into the chamber at predetermined levels. The test samples were irradiated with 6.2 W/m$^2$ UV radiation in the range of 300 to 400 nm from a UV lamp Model VL-6LM 365 & 312 nanometer wavelengths (BDH). Initial values and final values (after five minutes irradiation) of NO$_x$ were measured by a Nitrogen Oxides Analyzer Model ML9841B (Monitor Europe) connected to the sample chamber. The % reduction in NO$_x$ was measured as (ΔNO$_x$/Initial NO$_x$)×100. The results of these tests are shown and described in FIGS. 1 and 2.

The results of the examples indicate that the neutralized titanium dioxide sols exhibit a higher NO$_x$ reduction activity than the original un-neutralized alkaline titanium dioxide sol. In most all cases, the NO$_x$ reduction activities are increased as the amount of phosphoric acid added to the alkaline titanium dioxide sol is increased.

Figure 3:
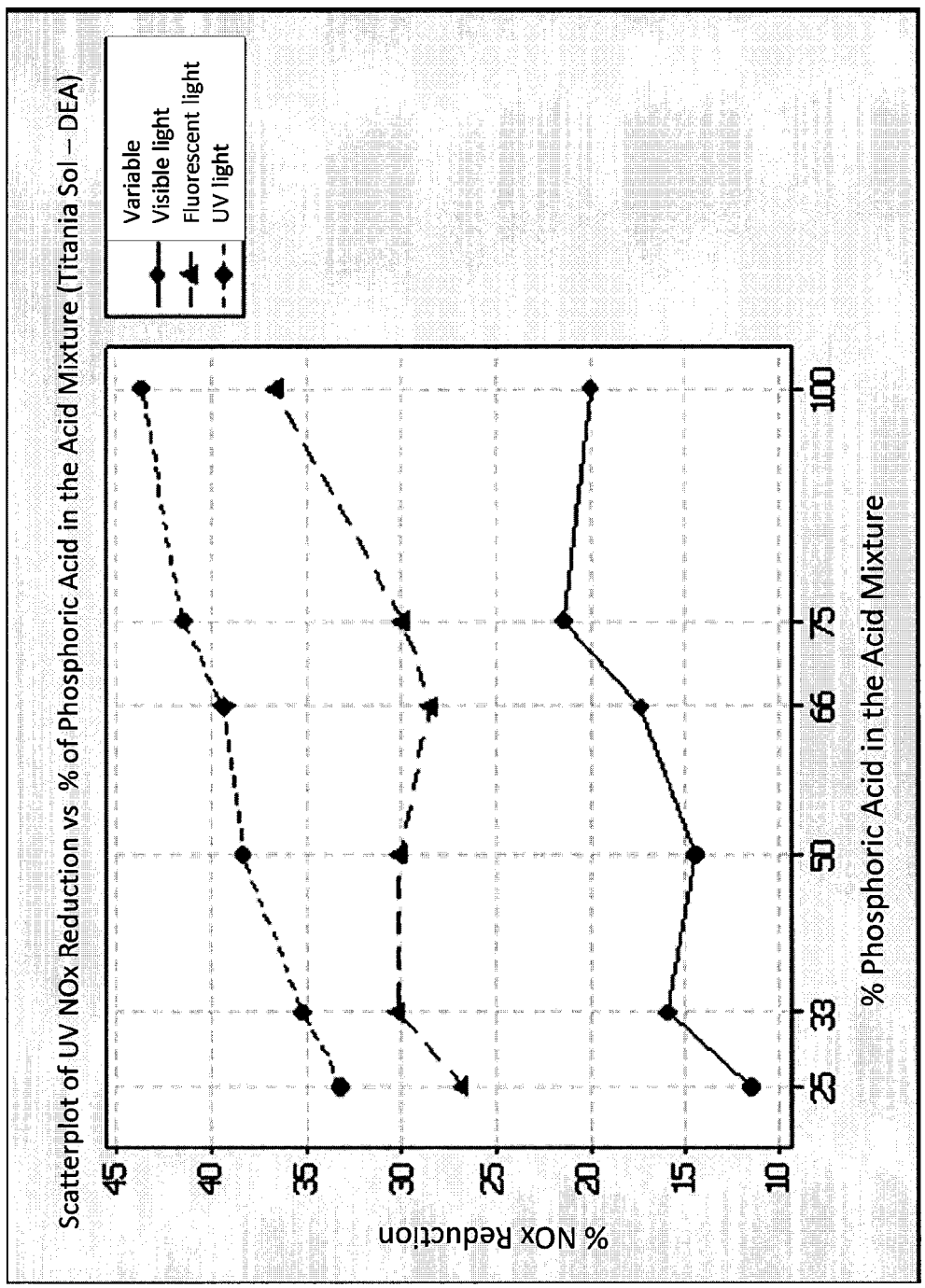
FIG. 3 is a graph comparing $NO_x$ reduction of an alkaline titanium dioxide sol containing DEA treated with different percentages of phosphoric acids combined with acetic acids under various light sources.
Figure 4:
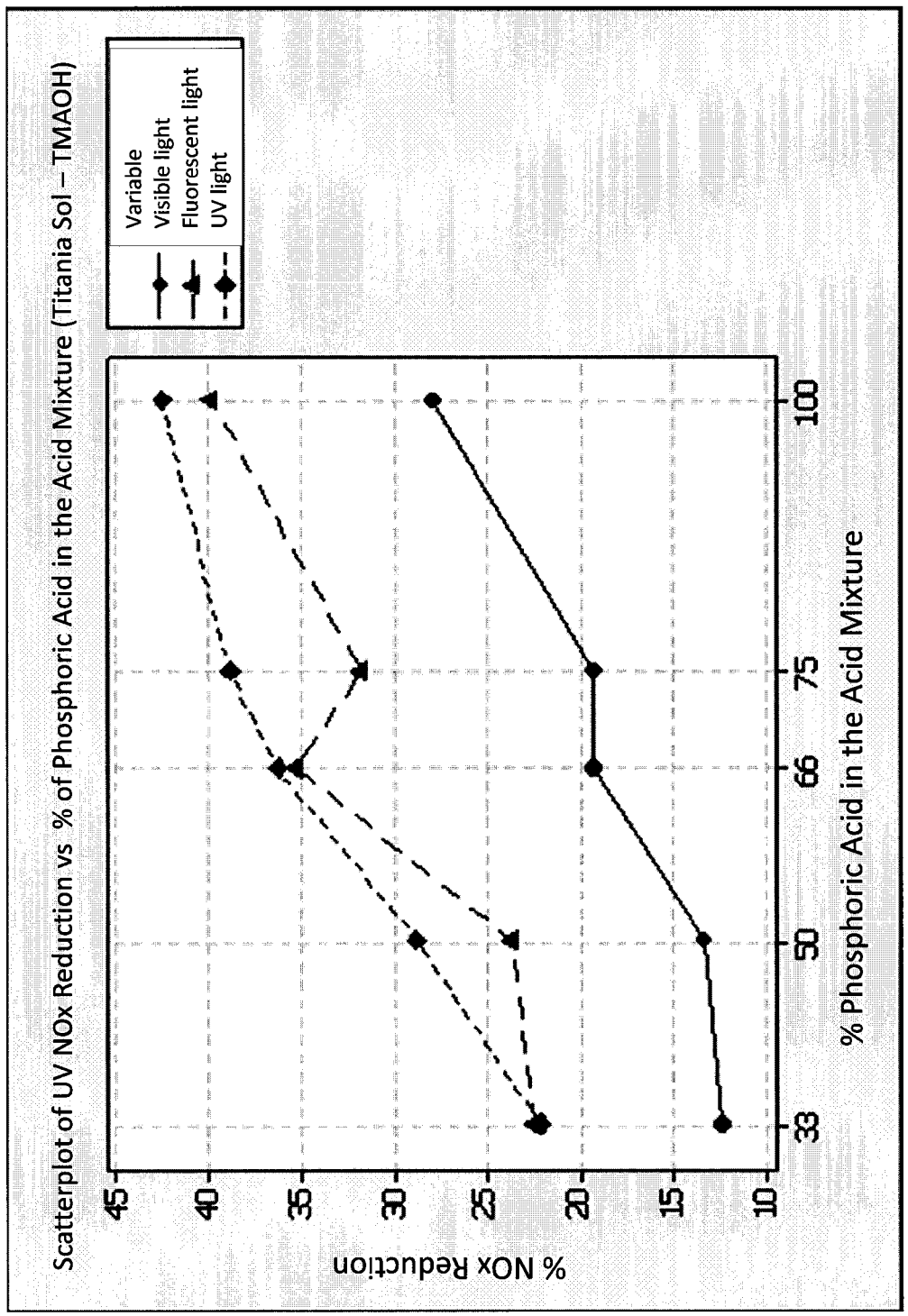
FIG. 4 is a graph comparing $NO_x$ reduction of an alkaline titanium dioxide sol containing TMAOH as a function of concentration of phosphoric acid combined with acetic acid under various light sources.

NO$_x$ removal was also studied under different lighting conditions and sources. In addition to UV, low intensity fluorescent strip lighting and visible light (as filtered through glass) were employed. FIGS. 3 and 4 show and describe the % of NO$_x$ reduction achieved using each of these different light sources. The results indicate that the neutralized titanium dioxide sol exhibits higher NO$_x$ reduction activities than the original un-neutralized alkaline titanium dioxide sol under all differing light sources.

Example 3

Figure 5:
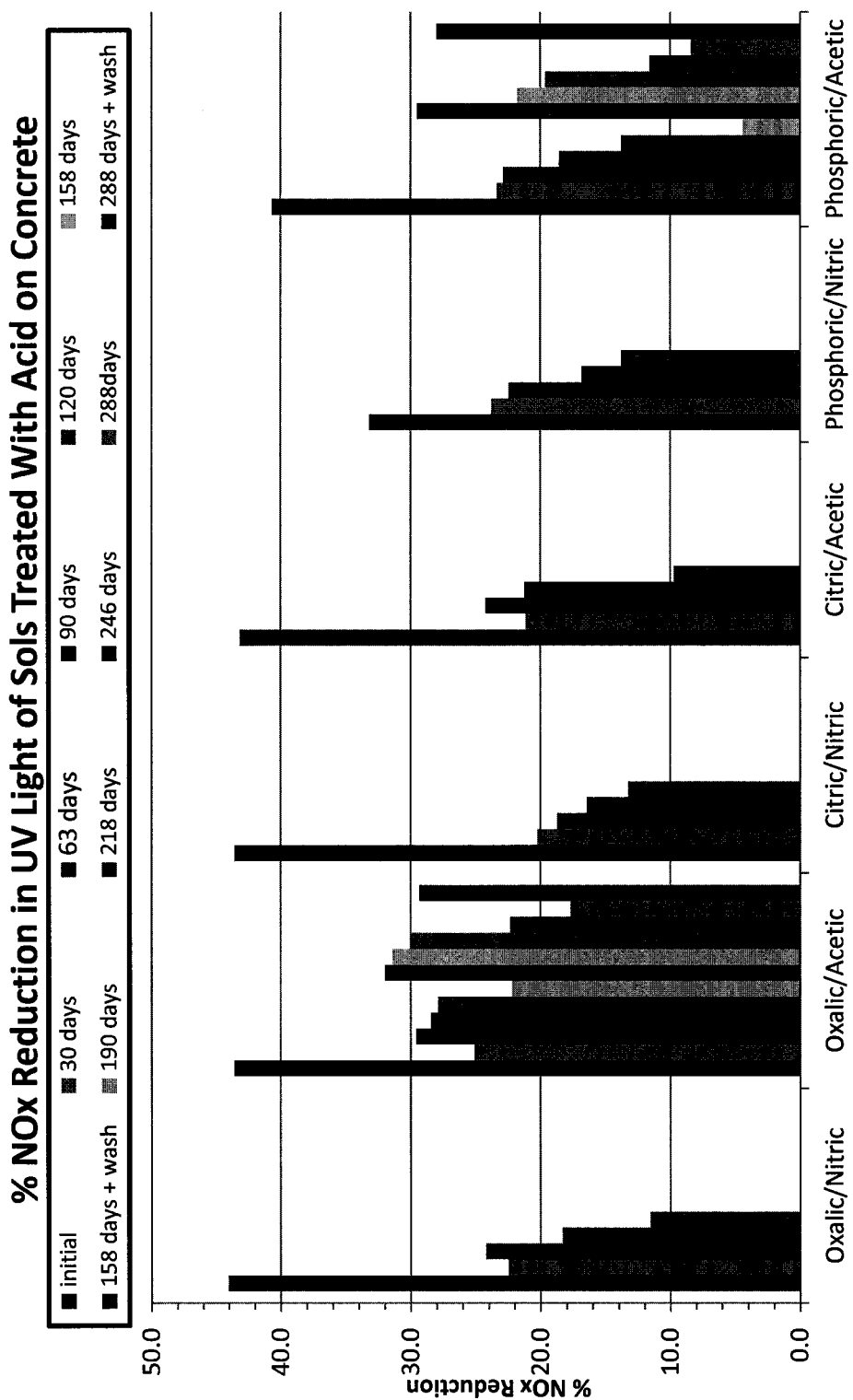
FIG. 5 is a graph comparing $NO_x$ reduction of an alkaline titanium dioxide sol containing DEA (diethyl amine) treated with various acids on concrete under UV radiation as a function of time.

In order to investigate the photocatalytic activity of coatings prepared from the sols according to the presently claimed and disclosed inventive concept(s), titania sols were prepared in the same manner as in Example 1, but instead of treatment with the phosphoric acid/acetic acid mixture of Example 1, such titania sols were treated with the following acid mixtures: oxalic acid/nitric acid, oxalic acid/acetic acid, citric acid/nitric acid, citric acid/nitric acid, phosphoric acid/nitric acid, and phosphoric acid/acetic acid, respectively. For the individual sols, either 1M oxalic acid or 1M citric acid or 1M phosphoric acid was added in an amount of 0.1 wt % based on the total weight of the sol; with pH adjustment of the sols to 8.5 through the addition of either nitric acid or acetic acid. Such acid treated sols were deposited as thin layers on concrete substrates (about 0.3 ml of sol on an 18 cm$^2$ area). The activity against NO$_x$ pollutants under UV radiation (6.2 W/m$^2$) was measured at various intervals over a period of about 288 days (activities for the oxalic/acetic and phosphoric/acetic acid treated sols were measured over the full 288 day period; whereas the period for activity measurement for the remaining sols was up to 120 days). The methodology for determining NO$_x$ reduction was substantially as described in U.S. Patent Pub. 2007/0167551, the disclosure of which is hereby incorporated by reference. The results of these tests are shown and described in FIG. 5.

Example 4

Figure 6:
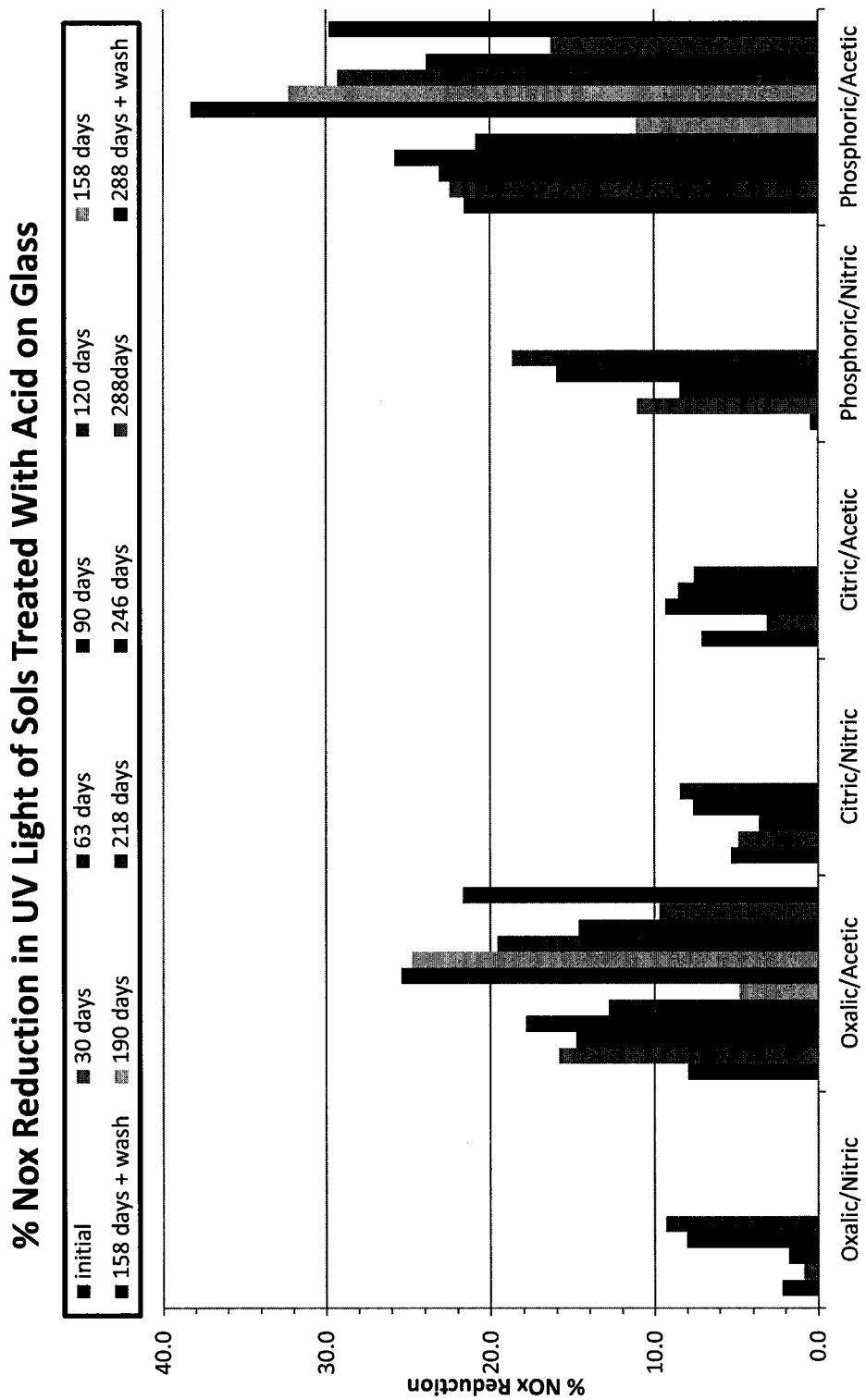
FIG. 6 is a graph comparing $NO_x$ reduction of an alkaline titanium dioxide sol containing DEA treated with various acids on glass substrate under UV radiation as a function of time.

In order to investigate the photocatalytic activity of coatings prepared from the sols according to the presently claimed and disclosed inventive concepts, the titania sols from Example 3 above were also deposited as thin layers on glass substrates (about 0.3 ml of sol on an 18 cm$^2$ area). The activity against NO$_x$ pollutants under UV radiation (2 W/m$^2$) was measured at various intervals over a period of about 288 days (activities for the oxalic/acetic and phosphoric/acetic acid treated sols were measured over the full 288 day period; whereas the period for activity measurement for the remaining sols was up to 120 days). The methodology for determining NO$_x$ reduction was substantially as described in U.S. Patent Pub. 2007/0167551, the disclosure of which is hereby incorporated by reference. The results of these tests are shown and described in FIG. 6.

Example 5

Figure 7:
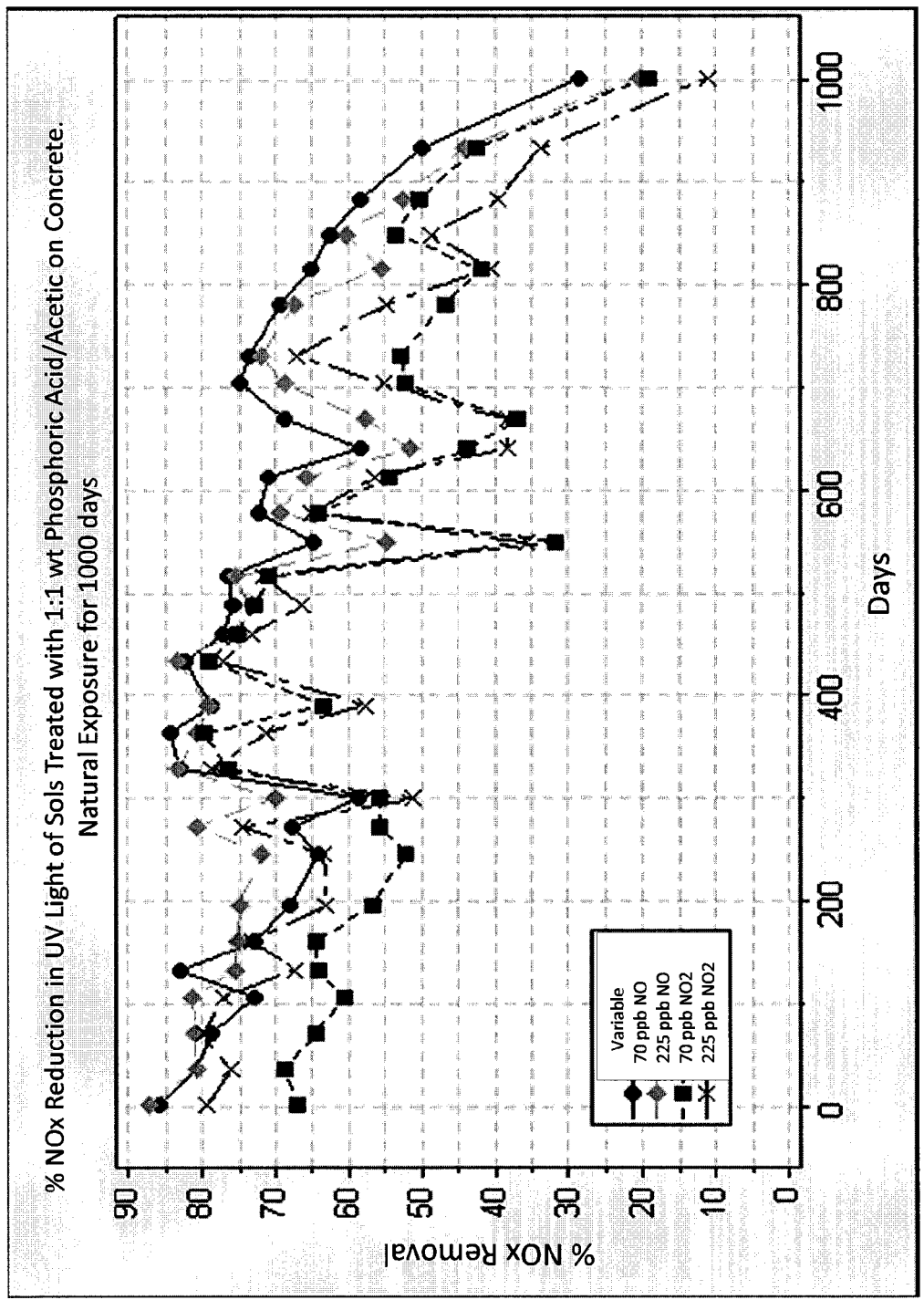
FIG. 7 is a graph comparing $NO_x$ reduction of an alkaline titanium dioxide sol containing DEA after neutralization with acetic & phosphoric acids on concrete at different initial NO exposures under UV radiation as a function of time.

In order to investigate the photocatalytic activity of coatings prepared from the sols according to the presently claimed and disclosed inventive concepts, the neutralized titania sol of Example 1 (having a 1:1 weight ratio of phosphoric acid to acetic acid) was deposited as thin layers on concrete (about 0.3 ml of 10% titania sol on an 18 cm² area). The thin layers on concrete were separately exposed to 225 ppb of NO, 225 ppb of NO$_2$, 70 ppb of NO, and 70 ppb of NO$_2$, respectively. The activity against NO$_x$ pollutants under UV radiation (6.23 W/m², 295-400 nm) was measured at various intervals over a period of about 1000 days. The methodology for determining NO$_x$ reduction was substantially as described in U.S. Patent Pub. 2007/0167551, the disclosure of which is hereby incorporated by reference. The results of these tests are shown and described in FIG. 7.

Example 6

Figure 8:
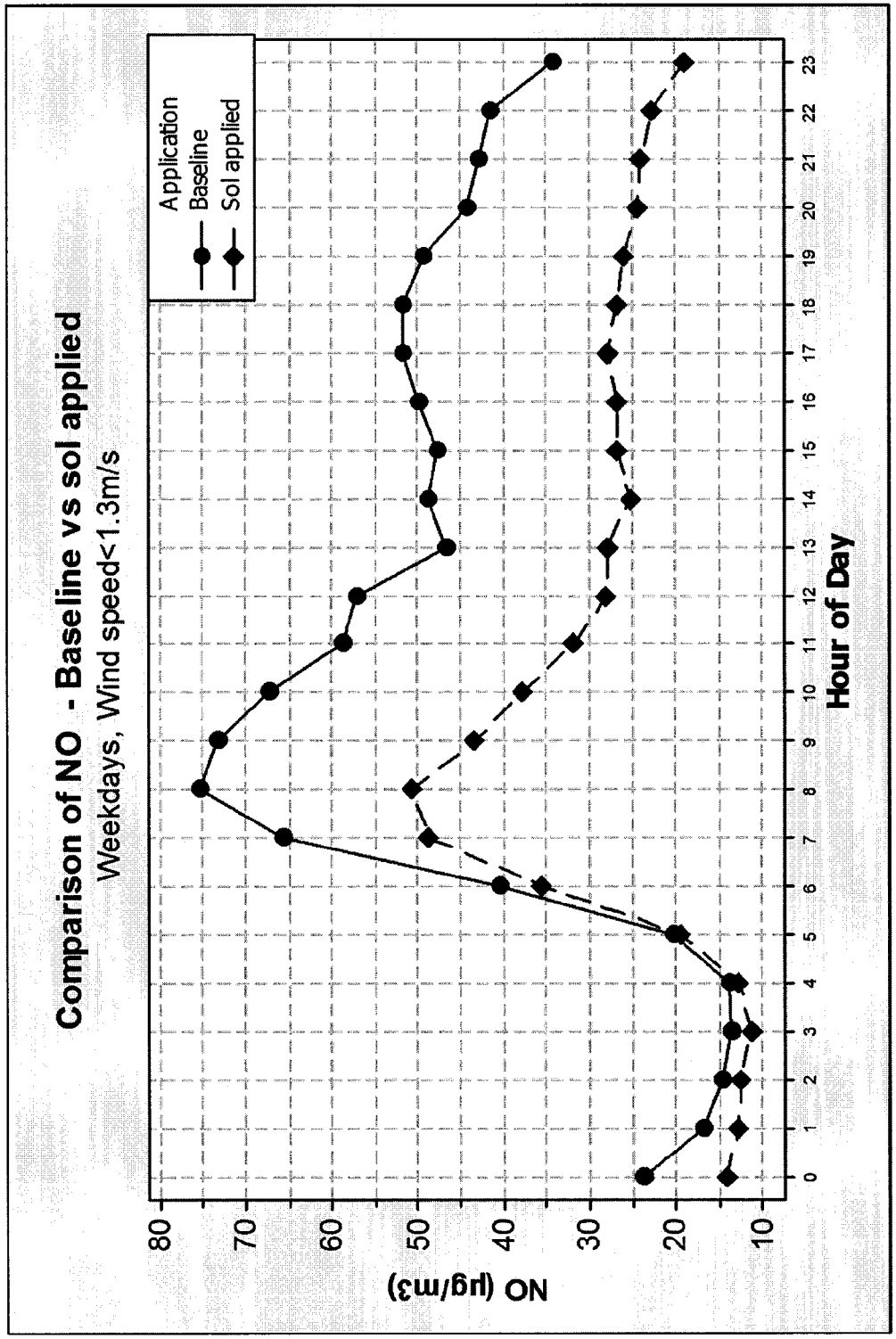
FIG. 8 is a graph comparing the amounts of NO in the baseline with those measured at a concrete wall coated with a neutralized alkaline titanium dioxide sol containing DEA as a function of time in the area of Camden-London, England.
Figure 9:
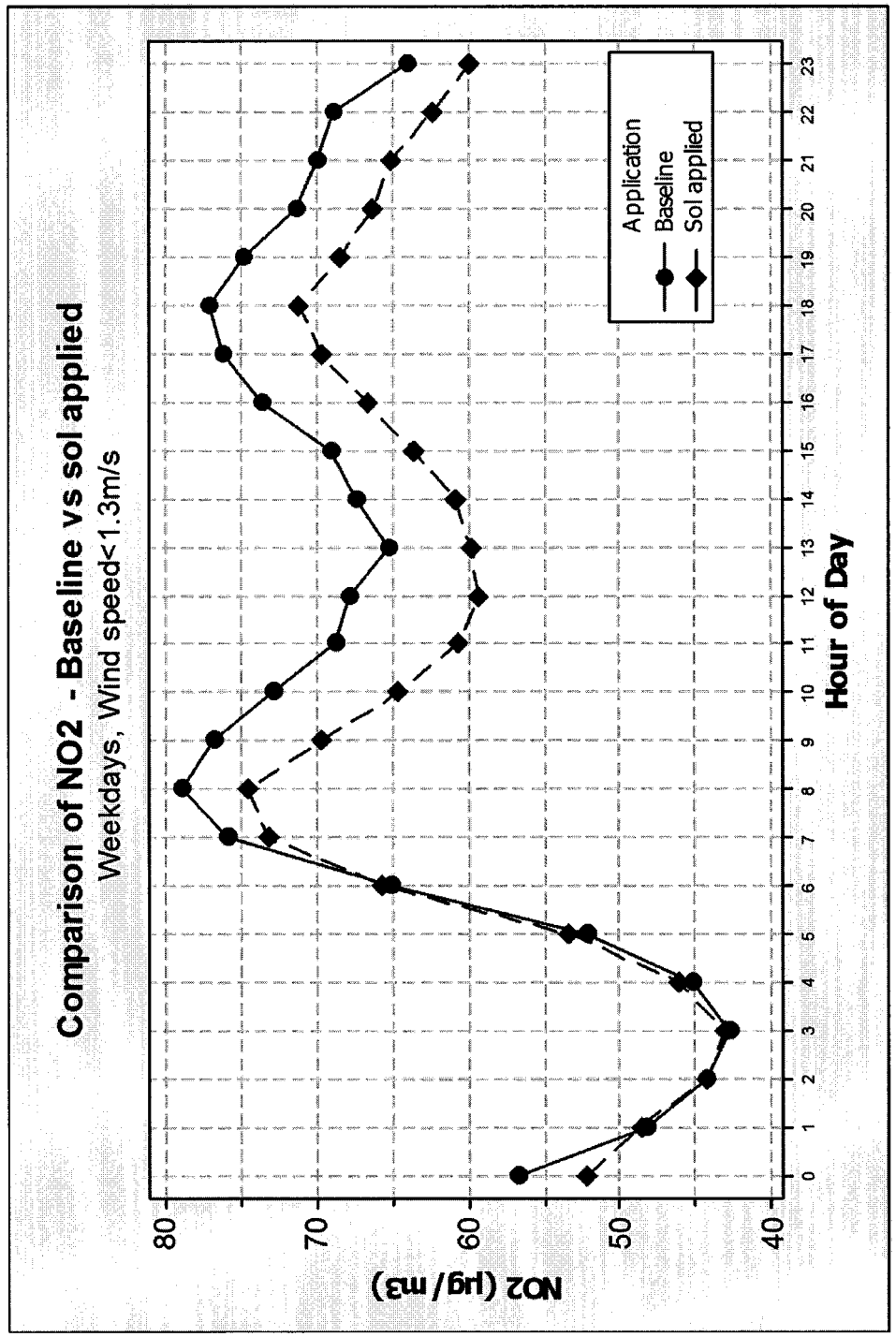
FIG. 9 is a graph comparing the amounts of $NO_2$ in the baseline with those measured at a concrete wall coated with a neutralized alkaline titanium dioxide sol containing DEA as a function of time in the area of Camden-London, England.

In order to investigate the photocatalytic activity of coatings prepared from the sols according to the presently claimed and disclosed inventive concepts, a thin layer of the neutralized titania sol of Example 1 (having a 1:1 weight ratio of phosphoric acid to acetic acid) which was diluted with water to form a 10 wt % titanium dioxide sol, was coated on a concrete wall (about 16 L of the 10 wt % titanium dioxide sol on a 135 m² area) located in an area of Camden-London, England. (GPS coordinates of 51.518904 N and 0120685 W). The air quality of the area was above the UK air quality standards in place as of the date of start and completion of the test. NO and NO$_2$ along with wind speed, wind direction, temperature and humidity were measured at 15 minute intervals. The NO and NO$_2$ were measured at a probe a distance of 15 cm from the wall. FIGS. 8 and 9 show the comparisons of the amounts of NO and NO$_2$ in baseline with those measured on the concrete wall coated with a neutralized alkaline titanium dioxide sol. The comparisons show the average amounts of NO and NO$_2$ measured at each hour of the day for each weekday over a period of more than 2 years. The comparisons also include only the NO and NO$_2$ data wherein the wind speed was less than 1.3 m/s. The titania sol kept high NO$_x$ removal activity even after more than two years exposure to the environment with high contents of NO and NO$_2$ in the atmosphere surrounding the coated substrate of the titania sols of the presently claimed and disclosed inventive concepts.

Example 7

In order to investigate the antibacterial activity of coatings prepared from the sols according to the presently claimed and disclosed inventive concepts, samples of the neutralized titania sol of Example 1 (having a 1:1 weight ratio of phosphoric acid to acetic acid) were doped with Ag or Zn as given in Table 2. Samples B, C and D were diluted such that the titanium dioxide weight % was 10%.

TABLE 2

Titanium Sols Used for Testing Antibacterial Activity

| Sample | TiO$_2$, wt % | Doped Metal | Amount of Doped Metal, ppm |
|---|---|---|---|
| A | 14.5 | Ag | 1000 |
| B | 10 | Ag | 1000 |
| C | 10 | Zn | 5000 |
| D | 10 | — | — |

The doped and undoped titania sols were coated on glass slides to test the antibacterial activity against *Staphylococcus aureus*. The test for antibacterial activity (due to photo-activity) was conducted using a procedure based on standard number BS ISO 27447:2009 promulgated by the ISO, which specifies a test method for determining the antibacterial activity of materials containing a photocatalyst or having photocatalytic films on their surface. The above described method was used to measure the enumeration of bacteria under irradiation of UV light. The standard was based on standard number ISO 22196:2007 (formally JIS Z 2801:2000). Generally, however, the antibacterial activity was measured by quantifying the survival of bacterial cells which have been held in intimate contact for 24 hours at 21° C. with a surface that contains an antibacterial agent. The antibacterial effect was measured by comparing the survival of bacteria on a treated material with that achieved on an untreated material.

The titania sols of Table 2 were applied to glass slides for study. Some slight modifications in certain parts of the method were necessary due to the hydrophobic nature of the materials. Samples were tested in duplicate against a suite of controls. A known amount of *Staphylococcus aureus* suspension, (—i.e., 0.05 ml of a suspension of the test organism (adjusted to contain approx 5×10⁵ cells in 0.05 ml))—was applied to the coated slides (coated samples) and on a "blank" slide (known to have no microbial activity and used as a control sample). The suspension was held in contact with 3 replicate coated samples and 6 replicate control samples. The 3 replicate coated samples and 3 of the 6 replicate control samples were then incubated for 24 hours at 21° C. and relative humidity of not less than 90%. After incubation, the samples were transferred to individual containers containing 10 ml of sterile neutralizer solution. The 3 replicate control samples were also processed in this manner prior to incubation in order to provide baseline or control data. Replicates of each surface coated with a titania sol solution were exposed to light (daylight fluorescent bulbs) while others were placed in the dark. Following these steps, bacterial counts were determined. The bacterial counts obtained (shown as a geometric mean), together with the antibacterial activities (shown as a Log$_{10}$ reduction) are given in Table 3.

The antibacterial activity after light exposure was calculated as follows:

$$R_L = \log(B_L/A) - \log(C_L/A) = \log(B_L/C_L)$$

The antibacterial activity in darkness was calculated as follows:

$$R_D = \log(B_D/A) - \log(C_D/A) = \log(B_D/C_D)$$

The photocatalytic antibacterial activity was calculated as follows:

$$R_P = \log(B_L/C_L) - \log(B_D/C_D)$$

where,
$R_L$ is the antibacterial activity after light exposure
$R_D$ is the antibacterial activity in darkness
$R_P$ is the photocatalytic antibacterial activity
A=mean bacterial count on a control sample at time zero
$B_L$=mean bacterial count on a control sample after 14 hours light exposure (+10 hours darkness)
$C_L$=mean bacterial count on a test piece after 14 hours light exposure (+10 hours darkness)
$B_D$=mean bacterial count on a control sample after 24 hours darkness
$C_D$=mean bacterial count on a test piece after 24 hours darkness

TABLE 3

Antibacterial Activity Test Results

| Sample | TiO$_2$ g/m$^2$ | Mean Bacterial Count | | | Antibacterial Activity | | Photocatalytic |
| --- | --- | --- | --- | --- | --- | --- | --- |
| | | Initial (×10$^5$) | 14/24 hrs light | 24 hrs dark | 14/24 hrs light | 24 hrs dark | Antibacterial Activity |
| Control | — | 6.2 | 5.3 × 10$^5$ | 4.9 × 10$^5$ | — | — | — |
| A | 0.75 | 6.2 | <10 | 1.2 × 10$^5$ | >4.7 | 0.61 | >4.1 |
| B | 2.5 | 6.2 | <10 | 7.4 × 10$^4$ | >4.7 | 0.82 | >3.9 |
| C | 5.0 | 6.2 | <10 | 7.3 × 10$^4$ | >4.7 | 0.82 | >3.9 |
| D | 11.0 | 6.2 | <10 | 3.5 × 10$^3$ | >4.7 | 2.1 | >2.6 |

Since a pass/fail criterion is not defined in the standard, the following criterion (as shown in Table 4) was used to comment on the level of activity determined.

TABLE 4

Antibacterial Activity Ranking

| Antibacterial Activity | Ranking | % Kill |
| --- | --- | --- |
| <1.5 | Poor | <96.8 |
| 1.5-2.0 | Borderline | 96.8-99.0 |
| 2.0-3.0 | Good | >99.0-99.9 |
| >3.0 | Excellent | >99.9 |

The test results indicate that all the titania sols of the presently claimed and disclosed inventive concepts (whether doped or undoped with a metal) demonstrate excellent antibacterial activities after exposure to daylight fluorescent bulbs.

Example 8

A first sol which is a neutralized titania sol of Example 1 (having a 1:1 weight ratio of phosphoric acid to acetic acid, and which was diluted to 10 wt % TiO$_2$ from 15 wt %) and a second sol (made from a different precursor and having a concentration of TiO$_2$ between 0.5 and 2.0%) were used to test the antibacterial activity against MRSA (Methicillin-resistant *Staphylococcus aureus*). Table 5 gives the compositions of the tested samples.

TABLE 5

Samples for Testing Antibacterial Activity against MRSA

| Sample | Coating | TiO$_2$ content, % |
| --- | --- | --- |
| 1 | First sol on blank Styrene/Acrylic on aluminum Q panel | 10 |
| 2 | First sol on stainless steel panel | 10 |
| 3 | Second sol on glass, Sample A | 0.5 |
| 4 | Second sol on glass, Sample B | 2 |
| 5 | First sol on glass, Sample C | 10 |

The test for antibacterial activity (due to photo-activity) was conducted using a procedure based on standard number BS ISO 27447:2009, which specifies a test method for determining the antibacterial activity of materials containing a photocatalyst or having photocatalytic films on the surface. The method was used to measure the enumeration of bacteria under irradiation of UV light. The standard was based on standard number ISO 22196:2007 (formally JIS Z 2801:2000).

The coated panels (Samples 1 and 2) were each cut into test pieces measuring approximately 35 mm×35 mm. Testing was carried out using *Staphylococcus aureus* ATCC 43300 (MRSA). For each test sample 0.1 ml of a suspension of the test organism (adjusted to contain approximately 5×10$^5$ cells in 0.1 ml) was placed on the coated surface of each of 6 replicates and on 6 replicate glass slides (used as controls and known to have no antibacterial activity). The suspension was held in intimate contact with the test and control surfaces using glass cover slips, 20 mm×20 mm in size. In order to provide a time zero inoculation level, an additional triplicate set of control samples were inoculated and washed off immediately, each into 10 ml of sterile neutralizer solution and microbial counts were determined to give a time zero count.

For each set of 6 replicates, 3 were exposed in a glass assay plate for 14 hours out of 24 hours under daylight fluorescent lamps. The assay plate containing the remaining 3 replicates of each test sample and control was wrapped in several layers of black plastic to prevent any light reaching the test films. This assay plate remained in darkness for the full 24 hours. Incubation for both sets of samples was at 21° C. and relative humidity of not less than 90%. After this time the test pieces were washed off, each into 10 ml of sterile distilled water, and bacterial counts were determined.

Samples 3-5 were tested using *Staphylococcus aureus* ATCC 43300 (MRSA). Because of the hydrophilic nature of the coated surfaces (which increased with increasing concentration of TiO$_2$), the method used previously was modified. An inoculum volume of 0.1 ml which is normally used, was found to spread too much on Sample C and could not be 'trapped' under the cover slip. A volume of 0.05 ml was used instead as this was considered to be the best compromise for use on all 3 surfaces.

A 0.05 ml quantity of a suspension of the test organism (adjusted to contain approximately 5×10$^5$ cells in 0.05 ml) was placed on the coated surface of each of 6 test sample replicates and on 6 replicate glass slides (used as the controls and known to have no antibacterial activity). The suspension was held in intimate contact with the test and control surfaces using glass cover slips, 20 mm×20 mm in size. In order to provide a time zero inoculation level, an additional triplicate set of control samples were inoculated (again using an inoculum volume of 0.05 ml) and washed off immediately, each into 10 ml of sterile neutralizer solution, and microbial counts were determined to give a time zero count.

As described previously, 3 replicates of each coated slide plus 3 controls were exposed to light and 3 replicates of each coated slide plus 3 controls were placed in darkness, following which bacterial counts were determined. The bacterial counts obtained (shown as a geometric mean), together with the antibacterial activities (shown as Log$_{10}$ reduction), are given in Tables 6 (Coated Panel) and 7 (Coated Glass Slides).

The calculations of antibacterial activity and photocatalytic antibacterial activity are the same as those described in Example 7.

TABLE 6

Antibacterial Activity Test Results: Coated Panel

| Sample | Mean Bacterial Count | | | Antibacterial Activity | | Photocatalytic |
|---|---|---|---|---|---|---|
| | Initial ($\times 10^5$) | 14/24 hrs light | 24 hrs dark | 14/24 hrs light | 24 hrs dark | 24 hrs Antibacterial Activity |
| Control | 6.2 | $3.1 \times 10^5$ | $3.3 \times 10^5$ | — | — | — |
| First sol on paint | 6.2 | $1.3 \times 10^3$ | $3.2 \times 10^5$ | 2.4 | 0.013 | 2.4 |
| First sol on steel | 6.2 | <10 | $1.2 \times 10^3$ | >4.5 | 2.4 | >2.1 |

TABLE 7

Antibacterial Activity Test Results: Coated Glass Slides

| Sample | Mean Bacterial Count | | | Antibacterial Activity | | Photocatalytic |
|---|---|---|---|---|---|---|
| | Initial ($\times 10^5$) | 14/24 hrs light | 24 hrs dark | 14/24 hrs light | 24 hrs dark | 24 hrs Antibacterial Activity |
| Control | 6.0 | $1.6 \times 10^5$ | $3.6 \times 10^5$ | — | — | — |
| Second sol Sample A | 6.0 | $1.9 \times 10^3$ | $1.6 \times 10^5$ | 1.9 | 0.35 | 1.6 |
| Second sol Sample B | 6.0 | $1.2 \times 10^3$ | $1.3 \times 10^5$ | 2.1 | 0.44 | 1.7 |
| First sol Sample C | 6.0 | <10 | $1.1 \times 10^5$ | >4.2 | 0.51 | >3.7 |

The criterion for analyzing the level of antibacterial activity is the same as listed in Table 4 of Example 7. Referring to Table 6, PCX-S7 on paint/Q panel demonstrated good antibacterial activity when exposed to light but very poor activity in darkness. Overall, good photocatalytic activity was demonstrated. PCX-S7 on stainless steel demonstrated excellent antibacterial activity when exposed to light and good activity in darkness. Overall, good photocatalytic activity against MRSA was demonstrated.

Referring to Table 7 Samples A and B (PCX-S2) demonstrated borderline to good antibacterial activity when exposed to light but poor activity in darkness. Overall, borderline photocatalytic activity against MRSA was demonstrated. Sample C(PCX-S7 on glass), however, demonstrated excellent antibacterial activity when exposed to light but poor activity in darkness. Overall, excellent photocatalytic activity against MRSA was demonstrated.

Example 9

Six paint samples and four sol samples (Sols 1-4) were tested for antibacterial activity against *Staphylococcus aureus*. The paint samples, labeled 1 to 6, contained different $TiO_2$ photocatalysts and were applied to aluminum Q panels and were prepared using the 1:1 phosphoric acid/acetic acid weight ratio sol of Example 1. The sol samples, labeled 1 to 4, were colloid dispersions, prepared in the same manner as the sols in Example 1, and applied to glass slides with $TiO_2$ loadings of approximately, 0.75, 2.5, 5.0 and 11 g/m², respectively.

The test for antibacterial activity (due to photo-activity) was conducted using a procedure based on standard number BS ISO 27447:2009, which specifies a test method for determining the antibacterial activity of materials containing a photocatalyst or having photocatalytic films on the surface. The method was used to measure the enumeration of bacteria under irradiation of UV light. The standard was based on standard number ISO 22196:2007 (formally JIS Z 2801:2000).

The paint coated panels were each cut into test pieces measuring approximately 35 mm×35 mm. Testing was carried out using *Staphylococcus aureus* ATCC 6538. A 0.1 ml quantity of a suspension of the test organism (adjusted to contain approximately $5\times10^5$ cells in 0.1 ml) was placed on the paint coated surface of each of 6 test sample replicates and on replicated glass slides (used as controls and known to have no antibacterial activity). The suspension was held in intimate contact with the test and control surfaces using glass cover slips, 20 mm×20 mm in size. In order to provide a time zero inoculation level, an additional triplicate set of control samples were inoculated and washed off immediately, each into 10 ml of sterile neutralizer solution and microbial counts were determined in order to provide a time zero count.

Of the 6 replicates of each sample, 3 were exposed in a glass assay plate for 14 hours out of 24 hours under daylight fluorescent lamps. The assay plate containing the remaining 3 replicates of each test sample was wrapped in several layers of black plastic to prevent any light from reaching the test films. This assay plate remained in darkness for the full 24 hours. Incubation for both sets of samples was at 21° C. and relative humidity of not less than 90%. After this time the test pieces were washed off, each into 10 ml of sterile distilled water, and bacterial counts were determined.

The titania sol coated glass slides were tested using *Staphylococcus aureus* ATCC 6538. Because of the hydrophilic nature of the titania sol coatings (which increased with increasing concentration of $TiO_2$), the method used above was modified. An inoculum volume of 0.1 ml which is normally used, was found to spread too much on Sol 4 and could not be 'trapped' under the cover slip. A volume of 0.05 ml was used instead as this was considered to be the best compromise for use on all 4 sol surfaces. A 0.05 ml quantity of a suspension of the test organism (adjusted to contain approximately $5\times10^5$ cells in 0.05 ml) was placed on the coated surface of each of 6 test sample replicates and on replicated glass slides (used as the control and known to have no antibacterial activity). The suspension was held in intimate contact with the test and control surfaces using glass cover slips, 20 mm×20 mm in size.

In order to provide a time zero inoculation level, an additional triplicate set of control samples were inoculated (again using an inoculum volume of 0.05 ml) and washed off immediately, each into 10 ml of sterile neutralizer solution, and microbial counts were determined to give a time zero count. As described previously, replicates of each titania sol surface were exposed to light and 3 were placed in darkness, following which bacterial counts were determined.

The bacterial counts obtained (shown as a geometric mean), together with the antibacterial activities (shown as $Log_{10}$ reduction), are provided in Tables 8 to 10. The calculations of antibacterial activity and photocatalytic antibacterial activity are the same as those described in Example 7.

TABLE 8

Antibacterial Activity Test Results: Paints 1-3

| Sample | Initial (×10⁵) | Mean Bacterial Count 14/24 hrs light | 24 hrs dark | Antibacterial Activity 14/24 hrs light | hrs dark | Photo-catalytic 24 Anti-bacterial Activity |
|---|---|---|---|---|---|---|
| Control | 5.4 | $3.1 \times 10^5$ | $3.2 \times 10^5$ | — | — | — |
| Paint 1 | 5.4 | $2.7 \times 10^5$ | $3.1 \times 10^5$ | 0.06 | 0.01 | 0.05 |
| Paint 2 | 5.4 | $2.6 \times 10^5$ | $2.9 \times 10^5$ | 0.08 | 0.04 | 0.04 |
| Paint 3 | 5.4 | $2.6 \times 10^5$ | $2.8 \times 10^5$ | 0.08 | 0.06 | 0.02 |

TABLE 9

Antibacterial Activity Test Results: Paints 4-6

| Sample | Initial (×10⁵) | Mean Bacterial Count 14/24 hrs light | 24 hrs dark | Antibacterial Activity 14/24 hrs light | hrs dark | Photo catalytic 24 Anti-bacterial Activity |
|---|---|---|---|---|---|---|
| Control | 6.1 | $5.4 \times 10^5$ | $5.8 \times 10^5$ | — | — | — |
| Paint 4 | 6.1 | $1.9 \times 10^5$ | $4.5 \times 10^5$ | 0.45 | 0.11 | 0.34 |
| Paint 5 | 6.1 | $1.9 \times 10^5$ | $5.5 \times 10^5$ | 0.45 | 0.02 | 0.43 |
| Paint 6 | 6.1 | $3.3 \times 10^5$ | $5.2 \times 10^5$ | 0.21 | 0.05 | 0.16 |

TABLE 10

Antibacterial Activity Test Results: Sols (SA)

| Sample | Initial (×10⁵) | Mean Bacterial Count 14/24 hrs light | 24 hrs dark | Antibacterial Activity 14/24 hrs light | hrs dark | Photo-catalytic 24 Anti-bacterial Activity |
|---|---|---|---|---|---|---|
| Control | 6.2 | $5.3 \times 10^5$ | $4.9 \times 10^5$ | — | — | — |
| Sol 1 | 6.2 | <10 | $1.2 \times 10^5$ | >4.7 | 0.61 | >4.1 |
| Sol 2 | 6.2 | <10 | $7.4 \times 10^4$ | >4.7 | 0.82 | >3.9 |
| Sol 3 | 6.2 | <10 | $7.3 \times 10^4$ | >4.7 | 0.82 | >3.9 |
| Sol 4 | 6.2 | <10 | $3.5 \times 10^3$ | >4.7 | 2.1 | >2.6 |

The criterion for analyzing the level of antibacterial activity is the same as listed on Table 4 in Example 8 above. Referring to Tables 8 and 9, the coated panel showed only very poor activity against *S. aureus*, both in darkness and after exposure to daylight fluorescent lamps, and hence significant photocatalytic antibacterial activity was not demonstrated.

Referring to Table 10, all 4 sol samples, however, demonstrated excellent antibacterial activity after exposure to daylight fluorescent bulbs. Sols 1 to 3 clearly demonstrated excellent photocatalytic antibacterial activity. The level of photocatalytic activity of Sol 4 was considered good, at the very least, although the actual level of photocatalytic activity could not be determined as this sample also demonstrated some antibacterial activity in the absence of light.

Example 10

Figure 10:
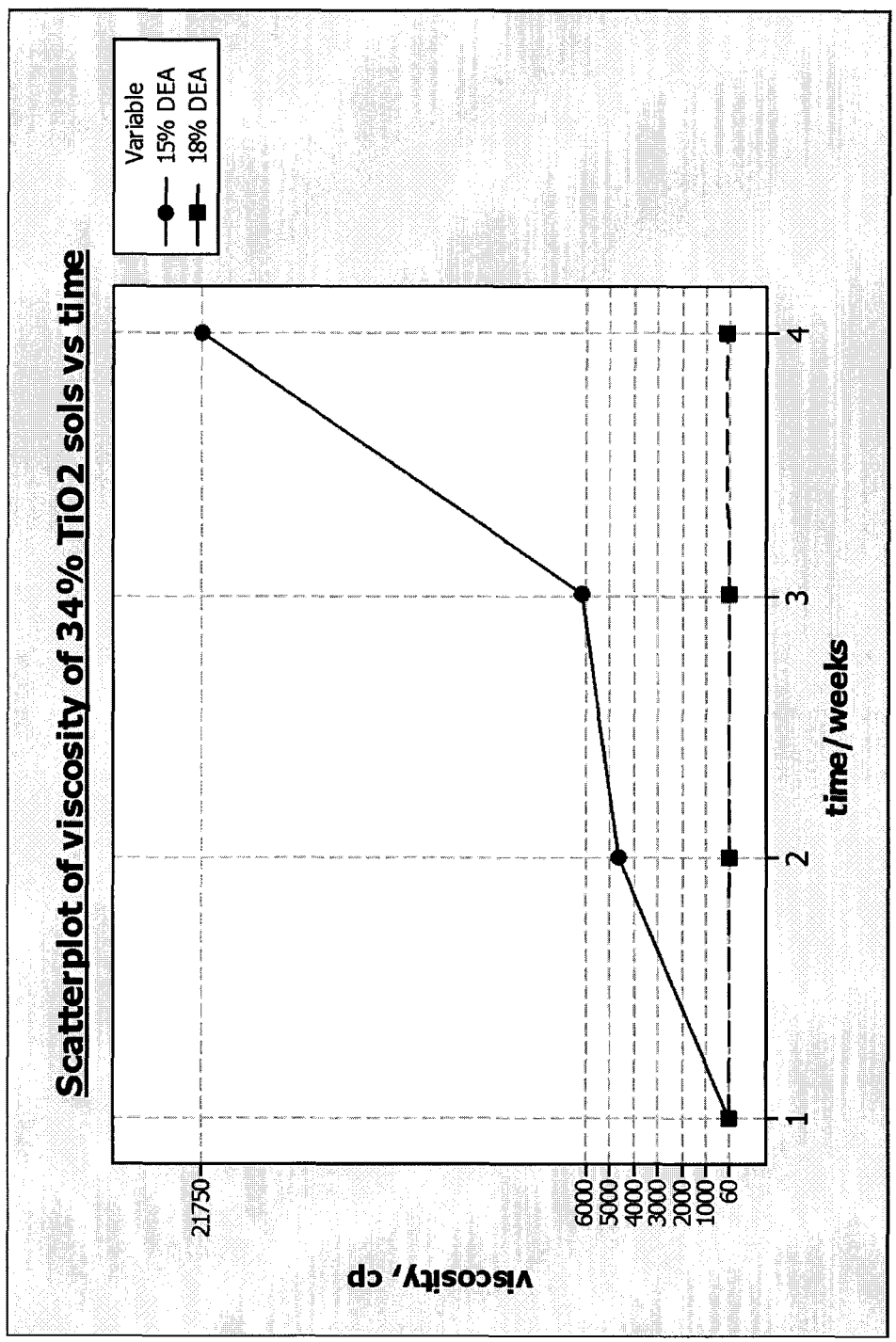
FIG. 10 is a graph comparing viscosity over time for alkaline titanium dioxide sols containing varying amounts of DEA.

In order to investigate the stability of coatings prepared from the sols according to the presently claimed and disclosed inventive concept(s), titania sols were prepared in the same manner as in Example 1, but with the following differences. Two sols were prepared without neutralization and contained 34 wt % titanium dioxide and 15 wt % and 18 wt % diethyl amine, respectively. FIG. 10 is a plot of viscosity over time for these unneutralized sols, and shows that use of 18 wt % diethyl amine results in improved stability as compared to the sol containing 15 wt % diethyl amine.

Figure 11:
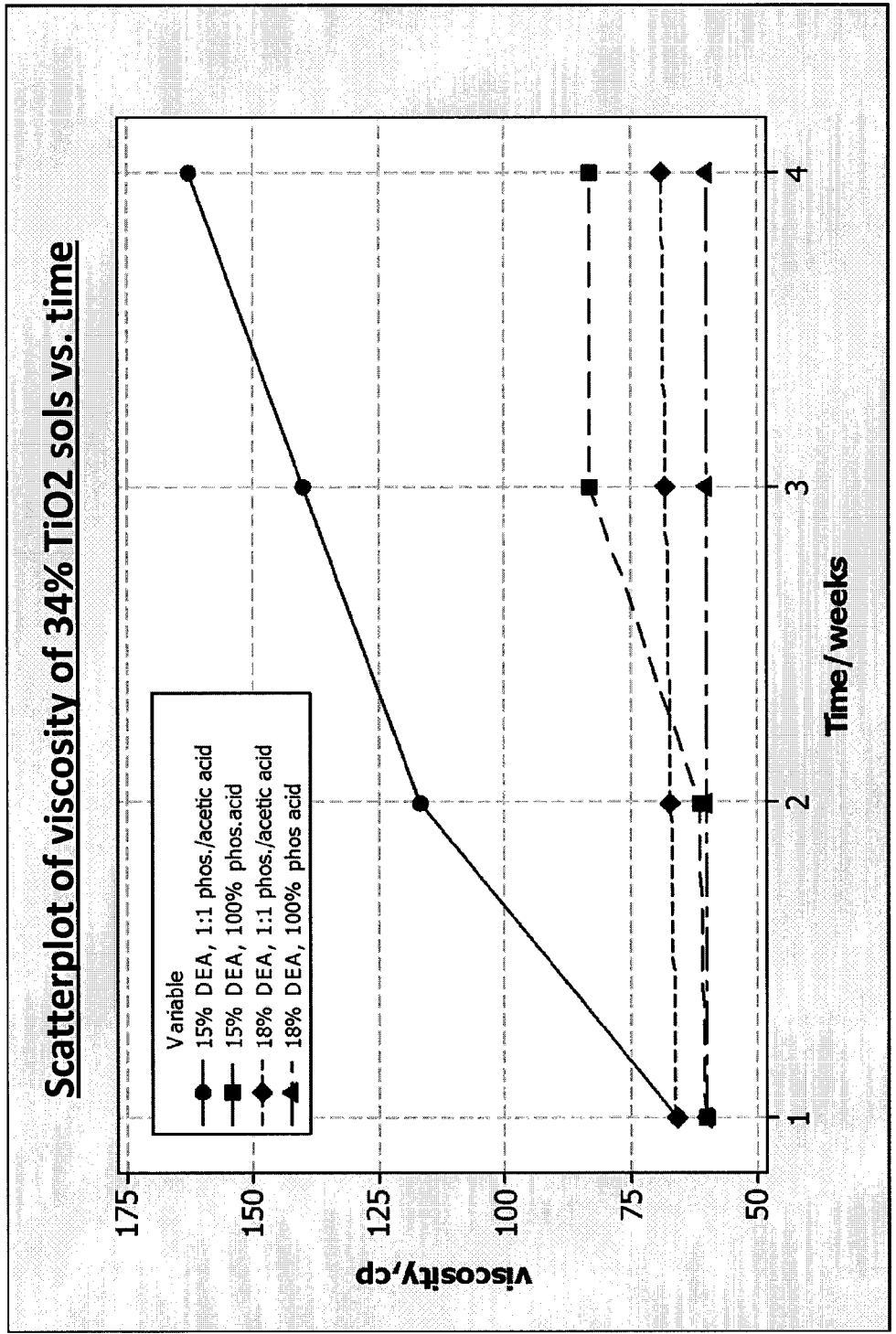
FIG. 11 is a graph comparing viscosity over time for alkaline titanium dioxide sols containing varying amounts of DEA treated with either phosphoric acid or a phosphoric/acetic acid mixture.

Four additional sols were prepared which also contained 34 wt % titanium dioxide, and with neutralization. The first neutralized sol contained 15 wt % diethyl amine and was neutralized with a 1:1 weight ratio of phosphoric acid to acetic acid. The second neutralized sol contained 15 wt % diethyl amine and was neutralized with 100 wt % phosphoric acid. The third neutralized sol contained 18 wt % diethyl amine and was neutralized with a 1:1 weight ratio of phosphoric acid to acetic acid. The fourth neutralized sol contained 18 wt % diethyl amine and was neutralized with 100 wt % phosphoric acid. Each of the sols were also washed with demineralized water. FIG. 11 is a plot of viscosity over time for these neutralized sols. FIG. 11 shows that the stability is greatly increased for the 15 wt % diethyl amine with neutralization using 100 wt % phosphoric acid as compared to neutralization with a 1:1 wt ratio of phosphoric acid to acetic acid. FIG. 11 also shows that the sols containing 18 wt % diethyl amine are more stable than the sols containing 15 wt % diethyl amine, and that the sol containing 18 wt % diethyl amine and neutralized with 100 wt % phosphoric acid is the most stable.

Example 11

Figure 12:
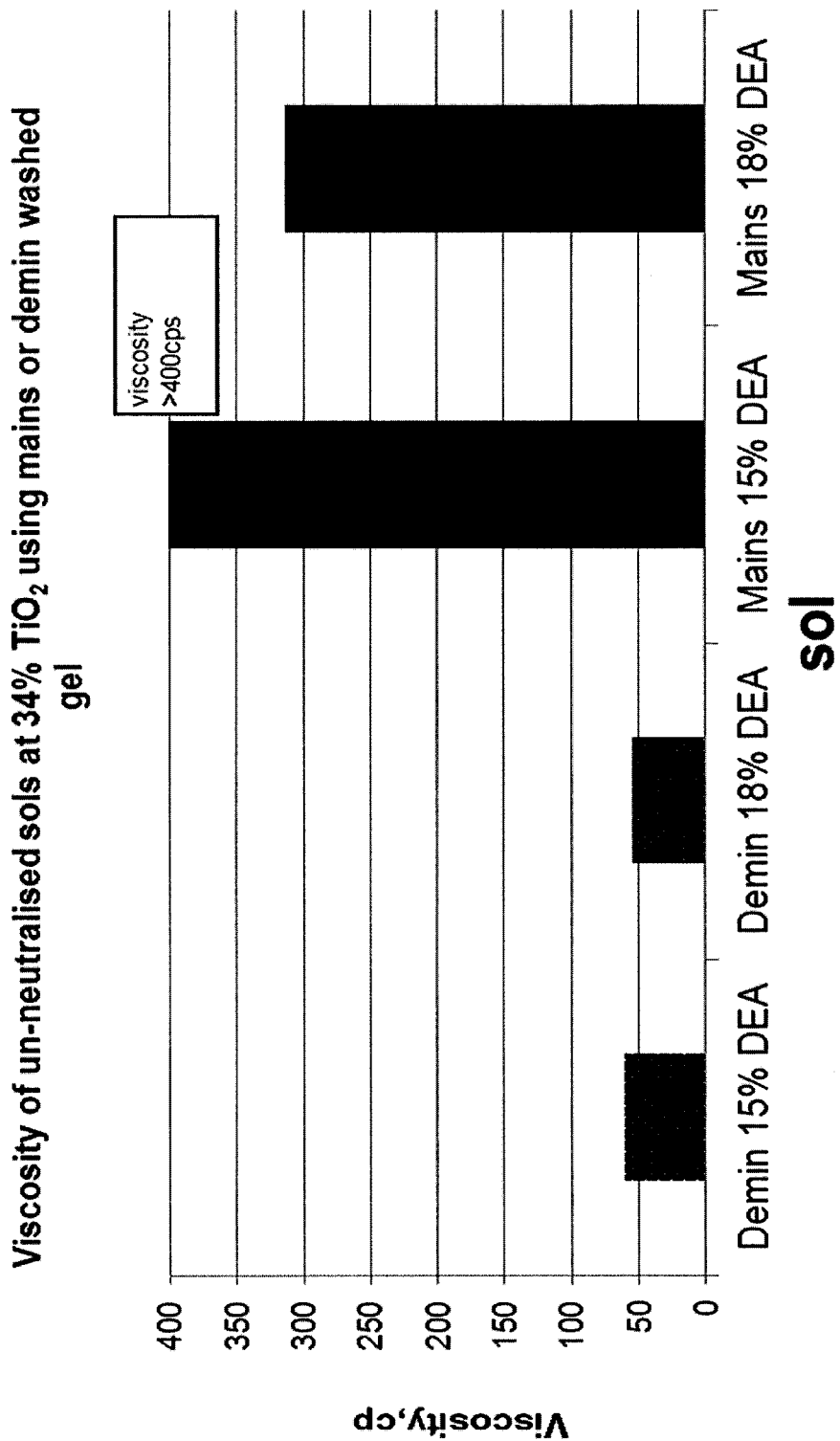
FIG. 12 is a graph comparing viscosity for alkaline titanium dioxide sols containing varying amounts of DEA and washed with either demineralized water or mains water.

In order to investigate the stability of coatings prepared from the sols according to the presently claimed and disclosed inventive concept(s), four titania sols were prepared in the same manner as in Example 1, but with the following differences. The four sols contained 34 wt % titanium dioxide, and were not neutralized. The first sol contained 15 wt % diethyl amine and was washed with demineralized water resulting in a calcium content of 71 ppm and a sodium content of less than 13 ppm. The second sol contained 18 wt % diethyl amine and was also washed with demineralized water resulting in a calcium content of 71 ppm and a sodium content of less than 13 ppm. The third sol contained 15 wt % diethyl amine and was washed with mains water resulting in a calcium content of 2535 ppm and a sodium content of 23 ppm. The fourth sol contained 18 wt % diethyl amine and was also washed with mains water resulting in a calcium content of 2535 ppm and a sodium content of 23 ppm. FIG. 12 is a plot of viscosity for each of the sols post washing. FIG. 12 shows that the stability is greatly increased for both the 15 wt % and the 18 wt % diethyl amine sols with washing using demineralized water as opposed to washing with mains water.

Example 12

Figure 13:
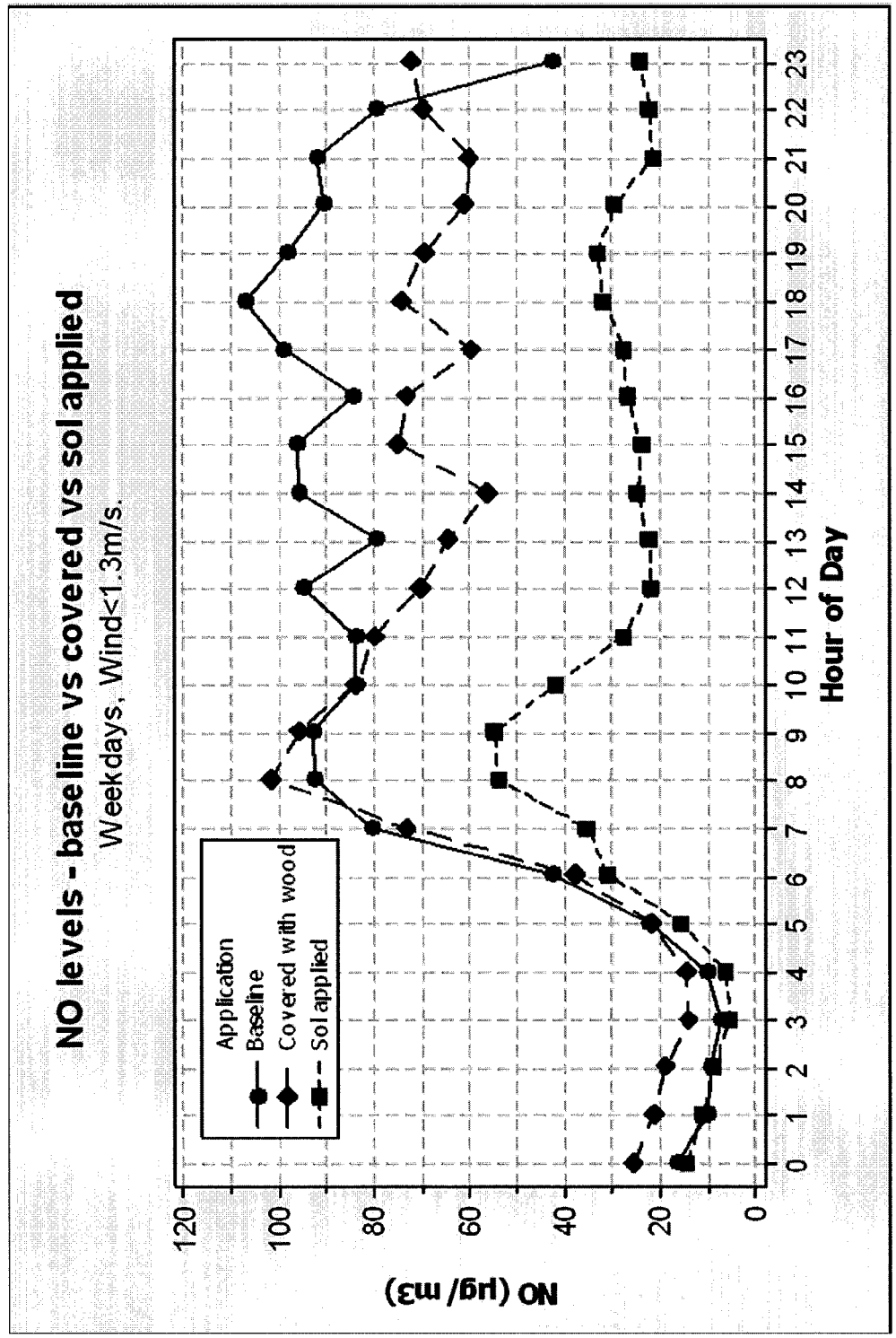
FIG. 13 is a graph comparing the amounts of NO in the baseline with those measured at a concrete wall coated with a neutralized alkaline titanium dioxide sol containing DEA, and with those measured at the concrete wall covered with wood, as a function of time in the area of Camden-London, England.
Figure 14:
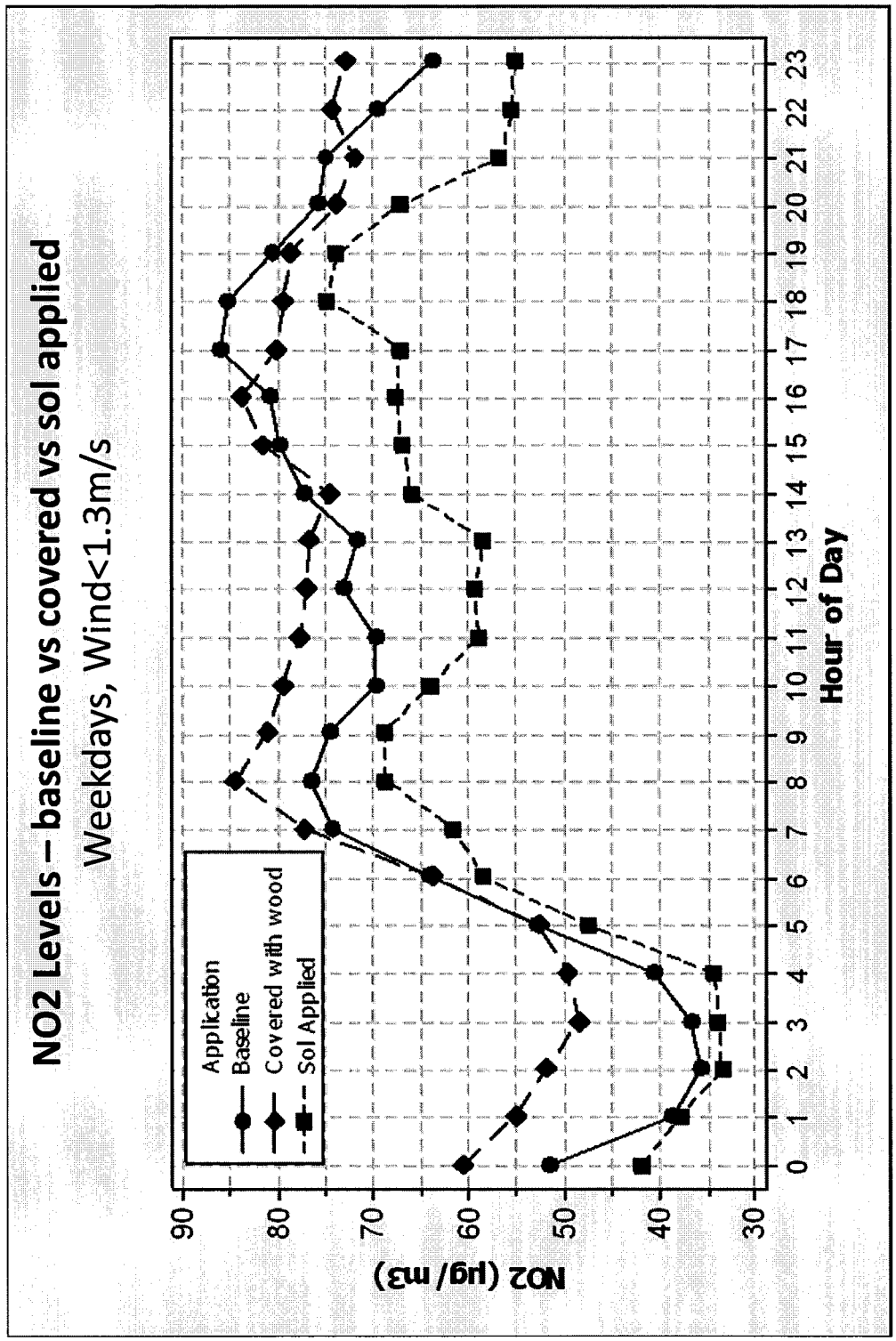
FIG. 14 is a graph comparing the amounts of $NO_2$ in the baseline with those measured at a concrete wall coated with a neutralized alkaline titanium dioxide sol containing DEA, and with those measured at the concrete wall covered with wood, as a function of time in the area of Camden-London, England.

In order to investigate the photocatalytic activity of coatings prepared from the sols according to the presently claimed and disclosed inventive concepts, a thin layer of the neutralized titania sol of Example 1 (having a 1:1 weight ratio of phosphoric acid to acetic acid) which was diluted with water to form a 10 wt % titanium dioxide sol, was coated on a concrete wall (about 16 L of the 10 wt % titanium dioxide sol on a 135 m² area) located in an area of Camden-London, England. (GPS coordinates of 51.518904 N and 0120685 W). NO and $NO_2$ along with wind speed, wind direction, temperature and humidity were measured at 15 minute intervals. The NO and $NO_2$ were measured at a probe a distance of 15 cm from the wall. Prior to the coating of the concrete wall with the titanium dioxide sol, baseline measurements of NO and $NO_2$ were acquired in year 1 for the months of September through December. Following the baseline measurements, the concrete wall was coated as described above and NO and $NO_2$ were measured in year 2 over the months of September through December. The concrete wall was then covered with wood to cover the titanium dioxide sol coating, and NO and $NO_2$ were measured in year 3 over the months of September through December. FIGS. 13 and 14 show the comparisons of the amounts of NO and $NO_2$ in baseline with those measured with the concrete wall coated with the titanium dioxide sol and with those measurements with the concrete wall covered with wood. The comparisons show the average amounts of NO and $NO_2$ measured at each hour of the day for each weekday for the months of September, October and December for years 1, 2 and 3, respectively. The data from November for each of those years was not used as the NO and $NO_2$ levels were exceptionally low at other nearby sites suggesting that there was another factor affecting the NO and $NO_2$ levels that month. The comparisons also include only the NO and $NO_2$ data wherein the wind speed was less than 1.3 m/s. FIGS. 13 and 14 show that coating the concrete wall with the titanium dioxide sol resulted in significant $NO_x$ removal activity over the baseline levels. FIGS. 13 and 14 also show that upon covering the coating for the following year, the $NO_x$ levels basically returned to the baseline levels, thus demonstrating the effectiveness of the titanium dioxide sol coating in $NO_x$ reduction.

Therefore, it has been demonstrated and shown that sols of titanium dioxide nanoparticles can be made and such sols are useful for providing transparent photocatalytic coatings on a substrate which are depolluting, self-cleaning, stain resistant, anti-bacterial, and/or anti-fungal/anti-microbial.

All references including patent applications and publications cited herein are incorporated herein by reference in their entirety and for all purpose to the same extent as if each individual publication or patent or patent application was specifically and individually indicated to be incorporated by reference in its entirety for all purposes. Many modifications and variations of the presently claimed and disclosed inventive concepts can be made without departing from its spirit and scope, as will be apparent to those skilled in the art. The specific embodiments described herein are offered by way of example only, and the presently claimed and disclosed inventive concepts is to be limited only by the terms of the appended claims, along with the full scope of equivalents to which such claims are entitled.

What is claimed is:

1. A method for preparing a neutral, stable and transparent photocatalytic titanium dioxide sol, comprising the steps of:
   (1) reacting a hydrous titanium dioxide gel with an alkaline alkylamine peptizing agent to provide a peptized alkaline titanium dioxide sol; and
   (2) neutralizing the peptized alkaline titanium dioxide sol with a combination of phosphoric acid and acetic acid to obtain a neutral, stable and transparent photocatalytic titanium dioxide sol comprising in the range of from about 0.5 to about 20 wt % titanium dioxide.

2. The method of claim 1, wherein the alkaline alkylamine peptizing agent is present in the neutral, stable and transparent photocatalytic titanium dioxide sol in an amount of at least about 7 wt %, based on the combined weight of the alkaline alkylamine peptizing agent and titanium dioxide.

3. The method of claim 1, wherein the alkaline alkylamine peptizing agent is present in the neutral, stable and transparent photocatalytic titanium dioxide sol in an amount of at least about 18 wt %, based on the combined weight of the alkaline alkylamine peptizing agent and titanium dioxide.

4. The method of claim 1 wherein the peptized alkaline alkylamine titanium dioxide sol is neutralized with a combination of phosphoric acid and acetic acid; wherein the weight ratio of the phosphoric acid to the acetic acid is in the range of from about 0.8:1 to about 1.2:1, and wherein the phosphoric acid and the acetic acid are simultaneously added to the peptized alkaline alkaline alkylamine titanium dioxide sol.

5. The method of claim 1, wherein the alkaline alkylamine is diethyl amine.

6. The method of claim 1, wherein the neutral, stable and transparent photocatalytic titanium dioxide sol comprises titanium dioxide crystallites having an average particle size of less than about 50 nm, at least 90% of which are in the anatase form.

7. The method of claim 1 wherein the neutral, stable and transparent photocatalytic titanium dioxide sol is doped with a metal, wherein the metal is selected from the group consisting of Ag, Zn, Mg, Sn, Fe, Co, Ni, Se, Ce, Cu and combinations thereof.

8. The method of claim 1 wherein the neutral, stable and transparent photocatalytic titanium dioxide sol is washed with demineralized water such that the concentration of calcium ions is less than about 71 ppm and the concentration of sodium ions is less than about 13 ppm in the resulting washed neutral, stable and transparent photocatalytic titanium dioxide sol, and wherein the filtrate conductivity is equal to or less than 500 µS.

9. The method of claim 8 wherein the viscosity of the washed neutral, stable and transparent photocatalytic titanium dioxide sol is less than about 100 centipoise after at least 4 weeks at room temperature.

* * * * *